United States Patent
Ahlfors

(10) Patent No.: US 10,712,352 B2
(45) Date of Patent: Jul. 14, 2020

(54) METHODS AND DEVICES FOR ASSESSING IN VIVO TOXIC LEVELS OF BILIRUBIN AND DIAGNOSING INCREASED RISK OF BILIRUBIN NEUROTOXICITY

(71) Applicant: NEOMETRIX DX, Renton, WA (US)

(72) Inventor: Charles Ahlfors, Renton, WA (US)

(73) Assignee: NEOMETRIX DX, Renton, WA (US)

( * ) Notice: Subject to any disclaimer, the term of this patent is extended or adjusted under 35 U.S.C. 154(b) by 0 days.

(21) Appl. No.: 16/540,781

(22) Filed: Aug. 14, 2019

(65) Prior Publication Data

US 2019/0383837 A1    Dec. 19, 2019

Related U.S. Application Data

(63) Continuation of application No. PCT/US2019/025423, filed on Apr. 2, 2019.

(60) Provisional application No. 62/652,266, filed on Apr. 3, 2018.

(51) Int. Cl.
*G01N 33/72* (2006.01)
*G01N 35/00* (2006.01)

(52) U.S. Cl.
CPC ....... *G01N 33/728* (2013.01); *G01N 35/0099* (2013.01); *G01N 2800/085* (2013.01); *G01N 2800/207* (2013.01); *G01N 2800/28* (2013.01); *G01N 2800/52* (2013.01)

(58) Field of Classification Search
CPC .................................................. G01N 33/728
USPC .......................................................... 702/19
See application file for complete search history.

(56) References Cited

U.S. PATENT DOCUMENTS

| | | |
|---|---|---|
| 7,416,896 B1 | 8/2008 | Ahlfors et al. |
| 2016/0245799 A1 | 8/2016 | Glezer et al. |

OTHER PUBLICATIONS

Young, International Search Report for PCT/US2019/025423 dated May 29, 2019.
Young, Written Opinion for PCT/US2019/025423 dated May 29, 2019.

Ahlfors et al., "Measurement of unbound bilirubin by the peroxidase test using Zone Fluidics" Clinica Chimica Acta, 2006, v, 365, p. 78-85.
Ahlfors et al., "Measurement of Plasma Unbound Unconjugated Bilirubin" Analytical Biochemistry, 2000, v 279, p. 130-135.
Ahlfors et al., "Effects of sample dilution, peroxidase concentration, and chloride ion on the measurement of unbound bilirubin in premature newborns" Clinical Biochemistry, 2007, v 40, p. 261-267.
Aviv Biomedical, Inc., Bili-4 Hematofluorometer accessed Sep. 2, 2016, p. 1-2.
Amin, Bilirubin Binding Capacity in the Preterm Neonate Clin Perinatol, 2016, v 43, p. 241-257.
Amin et al., "Newborn Jaundice Technologies: Unbound Bilirubin and Bilirubin Binding Capacity in Neonates" Semin Perinatol., 2001, v 35, n 3 , p. 134-140.
Huber et al., "Fluorescence Sensor for the Quantification of Unbound Bilirubin Concentrations" Clinical chemistry, 2012, v 58, n 5, p. 869-876.
Hegyi et al., "Unbound Free Fatty Acids from Preterm Infants Treated with Intralipid Decouples Unbound from Total Bilirubin Potentially Making Phototherapy Ineffective" Neonatology, 2013, p. 1-12.
Iskander et al., "Serum Bilirubin and Bilirubin/Albumin Ratio as Predictors of Bilirubin Encephalopathy" Pedicatrics, 2014, v 134, n 5, p. e1330-e1339.
Richieri et al., "Unbound free fatty acid levels in human serum" Journal of Lipid Research, 1995, v 36, p. 229-240.
Wennberg et al., "Toward Understanding Kernicterus: A Challenge to Improve the Management of Jaundiced Newborns" Pediatrics, 2006, v 117, n 2, p. 474-485.

*Primary Examiner* — Jerry Lin
(74) *Attorney, Agent, or Firm* — Greer, Burns & Crain, Ltd.; Gregory P. Einhorn

(57) ABSTRACT

In alternative embodiments are provided methods, devices and systems that use clinical data to determine whether bilirubin binding is normal in a newborn infant with hyperbilirubinemia in order to detect in vivo neurologically toxic levels of bilirubin and to determine whether treatment is needed to prevent a bilirubin-induced neurological injury (e.g. encephalopathy). In alternative embodiments, also provided are devices and systems comprising automated microfluid handling technologies such as zone fluidics systems to obtain a bilirubin binding panel. In alternative embodiments, also provided are methods for using the bilirubin binding panel to determine if treatments are needed to ameliorate, reverse, or prevent a bilirubin-induced neurological injury (e.g. encephalopathy) in an individual in need thereof such as a newborn with hyperbilirubinemia (jaundice), and for commencing the treatment, if needed.

19 Claims, 9 Drawing Sheets

METHODS AND DEVICES FOR ASSESSING IN VIVO TOXIC LEVELS OF BILIRUBIN AND DIAGNOSING INCREASED RISK OF BILIRUBIN NEUROTOXICITY

RELATED APPLICATIONS

This U.S. Utility Patent Application is a continuation of and claims the benefit of priority under 35 U.S.C. § 120 of Patent Convention Treaty (PCT) International Application PCT/US2019/025423, filed Apr. 2, 2019, which claims benefit of priority under 35 U.S.C. § 119(e) of U.S. Provisional Patent Application Ser. No. (USSN) 62/652,266 Apr. 3, 2018. The aforementioned applications are expressly incorporated herein by reference in its entirety and for all purposes. All publications, patents, patent applications cited herein are hereby expressly incorporated by reference for all purposes.

TECHNICAL FIELD

This invention generally relates to medicine, medical diagnostics and medical devices. In alternative embodiments, provided are methods, devices and systems for assessing and treating in vivo toxic levels of bilirubin, and diagnosing the relative risk for developing bilirubin encephalopathy, or, having a bilirubin encephalopathy, by processing clinical data to accurately determine whether bilirubin binding is normal in a patient. In alternative embodiments, provided are methods, devices and systems that use clinical data to determine whether bilirubin binding is normal in a newborn infant with hyperbilirubinemia in order to detect in vivo neurologically toxic levels of bilirubin and to determine whether treatment is needed to prevent a bilirubin-induced neurological injury such as encephalopathy. Also provided are computer-implemented methods for converting clinical laboratory data into a bilirubin binding panel that comprises conventional serum or plasma total bilirubin concentration ($B_{Total}$) and serum or plasma unbound bilirubin or free bilirubin concentration ($B_{Free}$) measurements at two $B_{Total}$, to calculate a novel, clinically relevant maximum $B_{Total}$ and capacity constant ($B_{Tmax}$), and its corresponding equilibrium association constant ($K_A$), in order to accurately obtain $B_{Free}$ at any $B_{Total} < B_{Tmax}$ using $$B_{Free} = \frac{B_{Total}}{K_A(B_{Tmax} - B_{Total})}.$$

In alternative embodiments, also provided are devices and systems comprising automated micro-fluid handling technologies such as zone fluidics systems, to obtain a bilirubin binding panel by measuring $B_{Total}$ and $B_{Free}$ in a serum or a plasma sample at two $B_{Total}$ and incorporating computer-implemented methods as provided herein to analyze these data and output for the bilirubin binding panel a $B_{Tmax}$ and $K_A$ to determine whether $B_{Free}$ has reached or exceeded a standard $B_{Free}$ ($B_{FreeStandard}$) in the relevant newborn population, and, if not to calculate the $B_{Total}$ at which that will occur using $$B_{Total} = \frac{B_{FreeStandard} \cdot K_A \cdot B_{Tmax}}{1 + (K_A \cdot B_{FreeStandard})}.$$

A $B_{Free} \geq B_{FreeStandard}$ or a $$B_{Total} \geq \frac{B_{FreeStandard} \cdot K_A \cdot B_{Tmax}}{1 + (K_A \cdot B_{FreeStandard})}$$

indicate the relative risk of a bilirubin-induced neurological injury in a newborn with hyperbilirubinemia is increased. In alternative embodiments, also provided are methods for treating, ameliorating, reversing or preventing a bilirubin-related pathology and for using methods as provided herein, including use of a bilirubin binding panel, to determine if treatments are needed to ameliorate, reverse, or prevent a bilirubin-induced neurological injury (e.g., encephalopathy) in an individual in need thereof such as a newborn with hyperbilirubinemia (jaundice).

BACKGROUND

About 60% of all newborns become visibly jaundiced during the first two weeks of life. The jaundice is due to a normal, transient accumulation of the yellow pigment unconjugated bilirubin IX-α (referred to as bilirubin henceforth), a product of hemoglobin catabolism. The bilirubin accumulation is due increased bilirubin production as fetal red blood cells have shorter life spans versus adult red blood cells and delayed bilirubin excretion as the metabolic pathways for eliminating bilirubin mature over the first few days of life. Therefore, a transiently elevated blood bilirubin level, referred to as hperbilirubinemia, that is often accompanied by visible jaundice, is a normal, usually harmless event in newborns during the first few days of life. However, bilirubin is neurotoxic, and in some circumstances causes severe neurological injury resulting in death or serious sequelae, and clinicians therefore closely monitor newborns with hyperbilirubinemia.

Neurologically toxic levels of bilirubin cause a spectrum of serious neurological injuries such as acute bilirubin encephalopathy resulting in death with kernicterus at autopsy (yellow staining of specific brain nuclei) or chronic neurological sequelae (also referred to as kernicterus) including choreoathetotic cerebral palsy, high tone hearing loss, paralysis of upward gaze, and yellow staining of the teeth. In addition, there is recent concern that bilirubin neurotoxicity contributes to other neurological disorders including auditory neuropathy spectrum disorder, apnea in premature newborns, and possibly autism. This spectrum of neurological damage is collectively referred to as a bilirubin-induced neurologic dysfunction (BIND).

BIND can be prevented or ameliorated by increasing bilirubin excretion from the body using phototherapy or the more risky and invasive procedure known as blood exchange transfusion in which the newborn's blood with high bilirubin levels is slowly removed and replaced by compatible donor blood with low bilirubin levels. Clinicians currently use the serum or plasma total bilirubin concentration ($B_{Total}$) as shown in Table 1 below for newborns less than 35 weeks (see, e.g., Maisels M J. et al. An approach to the management of hyperbilirubinemia in the preterm infant less than 35 weeks of gestation. J Perinatol 2012; 32:660).

TABLE 1

| Gestational Age (weeks) | $B_{Total}$ (mg/dL) | |
| --- | --- | --- |
| | Phototherapy | Exchange Transfusion |
| <28⁰ᐟ⁷ | 5-6 | 11-14 |
| 28-29⁶ᐟ⁷ | 6-8 | 12-14 |
| 30-31⁶ᐟ⁷ | 8-10 | 13-16 |
| 32-33⁶ᐟ⁷ | 10-12 | 15-18 |
| 34-34⁶ᐟ⁷ | 12-14 | 17-19 |

The ranges of treatment $B_{Total}$ used in TABLE 1 (versus using a single treatment $B_{Total}$) are based on clinical experience and expert opinion rather than evidence-based, and introduce considerable uncertainty as to when treatment is needed as illustrated in FIG. 1 where, for example, in newborns less than (<) 28 weeks gestation, exchange transfusion is considered at $B_{Total}$=11 mg/dL but not mandatory until $B_{Total}$ reaches 14 mg/dL. How does a clinician decide whether a newborn less than 28 weeks gestation and a $B_{Total}$=12 mg/dL needs an exchange transfusion? The uncertainties are even greater in newborns greater than or equal to (≥) 35 weeks gestation wherein there are no mandatory $B_{Total}$ for phototherapy or exchange transfusion, the latter being only being "considered" when the $B_{Total}$ reaches 25 mg/dL (see American Academy of Pediatrics, Management of hyperbilirubinemia in the newborn infant 35 or more weeks of gestation. Pediatrics 2004; 114:297-316). These uncertainties lead to excessive treatment resulting in significant social and financial costs, yet this approach has not eliminated BIND.

Ranges of treatment $B_{Total}$ are used, e.g. in TABLE 1 because $B_{Total}$ correlates poorly with BIND (e.g. see Watchko J F et al. The enigma of low bilirubin kernicterus in premature infants: why does it still occur, and is it preventable? Semin Perinatol 2014; 38: 397-406 and Ip S et al. An evidence-based review of important issues concerning neonatal hyperbilirubinemia. Pediatrics 2004; 114: e130). Since neither phototherapy or exchange transfusion are without risk (including death), newborns may suffer from BIND or complications from unnecessary treatments.

As illustrated in FIG. 2, measuring plasma bilirubin binding is important since only the non-albumin bound or free plasma bilirubin ($B_{Free}$) crosses capillaries and the blood-brain barrier to enter the tissues where the brain resides. The higher the $B_{Free}$ at any $B_{total}$, the higher the corresponding tissue levels of bilirubin with greater brain exposure to bilirubin and, therefore, the risk of BIND, as illustrated in FIG. 3. Bilirubin binding is highly variable in newborn plasma, and newborns with poor bilirubin binding will have relatively higher $B_{Free}$ and tissue bilirubin levels at any $B_{Total}$ compared to newborns with normal binding, since, when poor bilirubin is present, the accumulated bilirubin needed to reach a given $B_{Total}$ is greater, and the higher tissue bilirubin levels at that $B_{Total}$, increase the brain exposure to bilirubin and the risk of BIND relative to comparable newborns with normal bilirubin binding (see FIG. 2 and FIG. 3).

Recent studies document that BIND is predicted by $B_{Free}$=in newborns with hyperbilirubinemia that have similar $B_{Total}$ (see FIG. 3, and e.g. Amin S B, et al. Chronic auditory toxicity in late preterm and term infants with significant hyperbilirubinemia. Pediatrics 2017; 140: e20164009), validating adding bilirubin binding to the routine evaluation of these newborns. Furthermore, bilirubin binding is routinely measured in Japan and has been reported be very helpful clinically (e.g. see Morioka I et al. Serum unbound bilirubin as a predictor for clinical kernicterus in extremely low birth weight infants at a late age in the neonatal intensive care unit. Brain Dev 2015; 37:753).

$B_{Total}$ and $B_{Free}$ are commonly but mistakenly viewed as independent alternatives for guiding clinical care, with the misconception that $B_{Free}$ treatment criteria would somehow replace current $B_{Total}$ treatment criteria, e.g. TABLE 1. $B_{Total}$ and $B_{Free}$ are not independent but rather interdependent measurements, inextricably linked chemically with plasma bilirubin binding sites (e.g. albumin) through the law of mass action. The risk of BIND depends on how much bilirubin has accumulated and how it distributed between blood and tissue, which is determined by $B_{Free}$ (FIG. 2) which in turn is a mathematical function of the $B_{Total}$ and the concentration and inherent binding ability of plasma bilirubin binding sites (e.g. albumin) as described in detail below. A workable approach for incorporating bilirubin binding into clinical care is to quantify bilirubin binding in a manner that allows identification of those newborns with below, average or poor bilirubin binding and adjusting the current $B_{Total}$ treatment guidelines accordingly. This reduces the uncertainty inherent in using $B_{Total}$ alone to determine the risk of BIND (e.g. FIG. 1) by individualizing care.

Quantifying plasma bilirubin binding requires determining (1) the maximum amount of bilirubin that can be bound ($B_{Tmax}$) and (2) how tightly it can be bound, which is typically quantified using equilibrium association or dissociation constants. $B_{Tmax}$ depends on the concentration of functioning bilirubin binding sites and is often referred to as the bilirubin binding capacity or the $B_{Total}$ at which the binding sites are "saturated" with bilirubin (e.g. if the concentration of binding sites is 453 μmol/L, $B_{Tmax}$=26.5 mg/dL=453 μmol/L). How tightly bilirubin is bound at a binding site is quantified by a binding constant, e.g. an equilibrium association constant $K_n$, where n is the number of sites with different inherent abilities to bind bilirubin, and the constants representing each site are $K_1$, $K_2$ ... $K_n$. The chemical equilibrium is

$$(B_{Tmax} - (B_{Total} - B_{Free})) + B_{Free} \xrightleftharpoons{K_1, K_2, \ldots K_n} B_{Total} - B_{Free}$$

wherein $B_{Total}$-$B_{Free}$ is the concentration of bilirubin bound to binding sites and $B_{Tmax}$-($B_{Total}$-$B_{Free}$) is the concentration of the unoccupied (available) bilirubin binding sites. Albumin is known to have at least two bilirubin binding sites, and quantifying bilirubin binding using standard methods to obtain $B_{Tmax}$, and the corresponding equilibrium constants requires measurement of $B_{Free}$ at several $B_{Total}$ (see Jacobsen J. Binding of bilirubin to human serum albumin—Determination of the Dissociation Constants. FEBS Lett 1969; 5: 112-114). The significant testing time, large sample volumes, and complexity of data analysis preclude routine quantification of bilirubin binding in clinical laboratories using standard methods.

SUMMARY

In alternative embodiments, provided are methods, devices and systems for assessing in vivo toxic levels of bilirubin, and diagnosing the relative risk for developing a bilirubin-related pathology such as a neuropathy, e.g., an encephalopathy or bilirubin-induced neurological dysfunction (BIND), which can include encephalopathy, deafness, or choreoathetotic cerebral palsy, particularly in a newborn with hyperbilirubinemia (jaundice).

In alternative embodiments, methods, devices and systems as provided herein comprise processing and analyzing clinical data to accurately determine whether plasma bilirubin binding is normal and to assess the relative risk of BIND in a patient by coupling the Bilirubin Binding Panel (BBP) of tests: $B_{Total}$ and $B_{Free}$ measured before and after sample enrichment with bilirubin, $B_{Tmax}$, and $K_A$ with current $B_{Total}$ treatment guidelines as determined with instrument implementation with computer algorithms. These data provide two important new assessments of the risk of BIND at the current $B_{Total}$, the $B_{Free}$ for comparison with the standard risk $B_{Free}$ for the relevant population ($B_{FreeStandard}$) and the $B_{Total}$ at which $B_{FreeStandard}$ occurs $$\left(B_{Total} = \frac{B_{FreeStandard} \cdot K_A \cdot B_{Tmax}}{1 + K_A \cdot B_{FreeStandard}}\right).$$

If $B_{Free} = B_{FreeStandard}$ or $$B_{Total} = \frac{B_{FreeStandard} \cdot K_A \cdot B_{Tmax}}{1 + K_A \cdot B_{FreeStandard}},$$

the relative risk of BIND is increased in jaundiced newborns with significant hyperbilirubinemia (in alternative embodiments, the term "significant hyperbilirubinemia" is a hyperbilirubinemia that requires a treatment to maintain the health of the individual, e.g., a patient such as a newborn infant, or requires a treatment to lower the hyperbilirubinemia to improve the health of the individual and/or to prevent further negative effects of the individual's health because of the hyperbilirubinemia, or to ameliorate symptoms of hyperbilirubinemia).

In alternative embodiments, provided are methods (processes), devices and systems for quantifying how well plasma binds bilirubin comprising determining the maximum total bilirubin concentration ($B_{Tmax}$) and its associated equilibrium association constant ($K_A$).

wherein $$B_{Free} = \frac{B_{Total}}{K_A(B_{Tmax} - B_{Total})},$$

and $B_{Free}$ and $B_{Total}$ are the measured plasma concentrations of unbound or free bilirubin and total bilirubin, respectively, and optionally the method determines whether the risk of bilirubin neurotoxicity, optionally BIND, is increased, by first using a novel method to obtain $B_{Tmax}$ and $K_A$ in a patient by measuring $B_{Total}$ and $B_{Free}$ before ($B_{Total}$, $B_{Free}$) and after ($B_{Total\_2}$, $B_{Free\_2}$) bilirubin enrichment of a plasma sample to obtain two equations with two unknowns ($B_{Tmax}$ and $K_A$), that can be solved for $B_{Tmax}$ as shown below:

$$B_{Tmax} = \frac{B_{Total} B_{Total\_2}(B_{Free\_2} - B_{Free})}{B_{Toatal} B_{Free\_2} - B_{Total\_2} B_{Free}}$$

The calculated $B_{Tmax}$, $B_{Total}$, and $B_{Free}$ are then entered into $$B_{Free} = \frac{B_{Total}}{K_A(B_{Tmsx} - B_{Total})}$$

to obtain $$K_A = \frac{B_{Total}}{B_{Free}(B_{Tmsx} - B_{Total})},$$

or alternatively, $K_A$ is the negative intercept and $B_{Tmax}$ is the negative slope divided by the intercept of $$\frac{1}{B_{Free}} \text{ versus } \frac{1}{B_{Total}}$$

as the reciprocal of $$B_{Free} = \frac{B_{Total}}{K_A(B_{Tmsx} - B_{Total})}$$

is the linear equation $$\frac{1}{B_{Free}} = \frac{B_{Tmax} \cdot K_A}{B_{Total}} - K_A,$$

and then comparing $B_{Free}$ with the $B_{FreeStandard}$ occurring at the treatment $B_{Total}$ and, optionally, the median $B_{Tmax}$ and median $K_A$ for the comparable population, e.g.

$$B_{FreeStandard} = \frac{\text{Treatment } B_{Total}}{\text{median } K_A(\text{median } B_{Tmax} - \text{Treatment } B_{Total})}$$

as illustrated in FIG. 4 and determining the patient's $B_{Total}$ at which the $B_{FreeStandard}$ occurs, i.e. the $$B_{Total} = \frac{B_{FreeStandard} \cdot K_A \cdot B_{Tmax}}{1 + (K_A \cdot B_{FreeStandard})}.$$

If $B_{Free} = B_{FreeStandard}$ or $$B_{Total} = \frac{B_{FreeStandard} \cdot K_A \cdot B_{Tmax}}{1 + K_A \cdot B_{FreeStandard}}$$

the risk of

BIND warrants treatment irrespective of $B_{Total}$ (e.g., see Table 2, showing bilirubin binding in 31 newborns less than (<) 28 weeks gestation (see Ahlfors C E. et al., Bilirubin binding capacity and bilirubin binding in neonatal plasma E-PAS2017 2017: 2718.2715) wherein the

TABLE 2

|  | $B_{Total}$ mg/dL | $B_{Free}$ µg/dL | $B_{Total\_2}$ mg/dL | $B_{Free\_2}$ µg/dL | $B_{Tmax}$ mg/dL | $K_A$ dL/µg |
|---|---|---|---|---|---|---|
| Mean | 6.0 | 0.45 | 13.8 | 2.51 | 23.1 | 1.97 |
| SD | 2.2 | 0.35 | 4.9 | 2.11 | 18.8 | 2.23 |
| Range | 2.0-9.8 | 0.06-0.44 | 6.3-23.0 | 0.42-10.61 | 8.0-118.1 | 0.07-0.70 |

TABLE 2-continued

| | $B_{Total}$ mg/dL | $B_{Free}$ µg/dL | $B_{Total\_2}$ mg/dL | $B_{Free\_2}$ µg/dL | $B_{Tmax}$ mg/dL | $K_A$ dL/µg |
|---|---|---|---|---|---|---|
| Median | 6.0 | 0.35 | 13.7 | 1.93 | 22.0 | 1.16 |
| $25^{th}$-$75^{th}$ | 4.2-7.9 | 0.23-0.61 | 9.2-18.0 | 1.1-3.3 | 14.3-24.8 | 0.75-2.20 | median $B_{Tmax}$ is 22.0 mg/dL and median $K_A$ is 16 dL/µg, wherein optionally the patient is a newborn, wherein the $B_{FreeStandard}$ at the mandatory phototherapy $B_{Total}$ of 6 mg/dL (Table 1) and optionally, the median $B_{Tmax}$ and $K_A$ for newborns less than (<) 28 weeks gestation (Table 1) would be $$B_{FreeStandard} = \frac{\text{Treatment } B_{Total}}{\text{median } K_A(\text{median } B_{Tmax} - \text{Treatment } B_{Total})} =$$

$$\frac{6 \frac{mg}{dL}}{1.16 \frac{dL}{\mu g}\left(22.0 \frac{mg}{dL} - 6 \frac{mg}{dL}\right)} = 0.32 \ \mu g/dL$$

as illustrated in FIG. 4, and the $B_{FreeStandard}$ at the mandatory exchange transfusion $B_{Total}$ of 14 mg/dL for newborns less than (<) 28 weeks gestation (Table 1) would be $$B_{FreeStandard} = \frac{14 \frac{mg}{dL}}{1.16 \frac{dL}{\mu g}\left(22.0 \frac{mg}{dL} - 14 \frac{mg}{dL}\right)} = 1.51 \ \mu g/dL$$

as illustrated in FIG. 4. A newborn in this population with a $25^{th}$ percentile $B_{Tmax}$ (14.3 mg/dL) and $K_A$ (0.75 dL/µg), i.e. poor bilirubin binding, would reach the phototherapy and exchange transfusion $B_{FreeStandard}$ of 0.32 µg/dL and 1.51 µg/dL, respectively, at $$B_{Total} = \frac{B_{FreeStandard} \cdot K_A \cdot B_{Tmax}}{1 + (K_A \cdot B_{FreeStandard})} = \frac{0.32 \frac{\mu g}{dL} \cdot 0.75 \frac{dL}{\mu g} \cdot 14.3 \frac{mg}{dL}}{1 + \left(0.75 \frac{dL}{\mu g} \cdot 0.32 \frac{\mu g}{dL}\right)} =$$

2.8 mg/dL and $B_{Total} = \frac{B_{FreeStandard} \cdot K_A \cdot B_{Tmax}}{1 + (K_A \cdot B_{FreeStandard})} =$ $$\frac{1.51 \frac{\mu g}{dL} \cdot 0.75 \frac{dL}{\mu g} \cdot 14.3 \frac{mg}{dL}}{1 + \left(0.75 \frac{dL}{\mu g} \cdot 1.51 \frac{\mu g}{dL}\right)} = 7.6 \ mg/dL,$$

respectively, well below the current phototherapy $B_{Total}$ threshold of 5 mg/dL and exchange transfusion threshold of 11 mg/dL in Table 1. On the other hand, a newborn in this population with a $75^{th}$ percentile $B_{Tmax}$ (24.8 mg/dL) and $K_A$ (2.20 dL/µg), i.e. excellent bilirubin binding, would reach the phototherapy and exchange transfusion $B_{FreeStandard}$ of 0.32 µg/dL and 1.51 µg/dL, respectively, at phototherapy $$B_{Total} = \frac{B_{FreeStandard} \cdot K_A \cdot B_{Tmax}}{1 + (K_A \cdot B_{FreeStandard})} = \frac{0.32 \frac{\mu g}{dL} \cdot 2.20 \frac{dL}{\mu g} \cdot 24.8 \frac{mg}{dL}}{1 + \left(2.20 \frac{dL}{\mu g} \cdot 0.32 \frac{\mu g}{dL}\right)} = 10.2 \ mg/dL$$

and exchange transfusion $$B_{Total} = \frac{B_{FreeStandard} \cdot K_A \cdot B_{Tmax}}{1 + (K_A \cdot B_{FreeStandard})} = \frac{1.51 \frac{\mu g}{dL} \cdot 2.20 \frac{dL}{\mu g} \cdot 24.8 \frac{mg}{dL}}{1 + \left(2.20 \frac{dL}{\mu g} \cdot 1.51 \frac{\mu g}{dL}\right)} = 19.1 \ mg/dL,$$

well above the current phototherapy $B_{Total}$ threshold of 5 mg/dL and $B_{Total}$ exchange transfusion threshold of 11 mg/dL in Table 1.) Two newborns with the same $B_{Total}$ but significantly different abilities to bind bilirubin will be at significantly different risks of BIND, and that difference can only be detected by measuring bilirubin binding. A newborn less than (<) 28 weeks gestation with $25^{th}$ percentile $B_{Tmax}$ (14.3 mg/dL) and $K_A$ (0.75 dL/µg), i.e. poor bilirubin binding, and a $B_{Total}$ of 7.6 mg/dL has reached the $B_{FreeStandard}$ for exchange transfusion (1.51 µg/dL) but without measuring bilirubin binding an unsuspecting clinician following current $B_{Total}$ treatment guidelines (Table 1), would only administer phototherapy and not consider exchange transfusion.

In alternative embodiments, methods as provided herein further comprise assessing the need for hyperbilirubinemia treatment in a patient at any $B_{Total}$ (irrespective of whether current clinical practice deems treatment should be considered) by comparing a the $B_{Free}$ in a patient versus the $B_{FreeStandard}$ in a comparable population (e.g. wherein optionally a comparable population is a population of the same gestational ages as shown in Table 1), wherein a $B_{Free}$ in the patient equal to or greater than the $$B_{FreeStandard} = \frac{\text{Treatment } B_{Total}}{\text{median } K_A(\text{median } B_{Tmax} - \text{Treatment } B_{Total})}$$

as illustrated in FIG. 4 or a $B_{Total}$ equal to or greater than $$\frac{B_{FreeStandard} \cdot K_A \cdot B_{Tmax}}{1 + (K_A \cdot B_{FreeStandard})}$$

(e.g. for newborns less than (<) 28 weeks gestation, the $B_{FreeStandard}$ at the mandatory exchange transfusion $B_{Total}$ of 14 mg/dL (Table 1), and optionally the median $B_{Tmax}$ (22.0 mg/dL) and $K_A$ (1.16 dL/µg) (Table 2) is $$B_{FreeStandard} = \frac{B_{Total}}{K_A(B_{Tmax} - B_{Total})} =$$

$$\frac{14\ mg/dL}{1.16\ dL/\mu g\ (22.0\ mg/dL - 14\ mg/dL)} = 1.51\ \mu g/dL,$$

indicates a greater risk of BIND at the mandatory treatment $B_{Total}$ (e.g. for newborns less than (<) 28 weeks gestation, the $B_{Free}$ at the 25$^{th}$ percentile $B_{Tmax}$ (14.3 mg/dL) and $K_A$ (0.75 dL/µg) per Table 2 and the mandatory exchange transfusion $B_{Total}$ of 14 mg/dL per Table 1 is $$B_{Free} = \frac{B_{Total}}{K_A(B_{Tmax} - B_{Total})} =$$

$$\frac{14\ mg/dL}{0.75\ dL/\mu g\ (14.3\ mg/dL - 14\ mg/dL)} = 62.2\ \mu g/dL,$$

over 40 times than $B_{FreeStandard}$=1.51 µg/dL) and that at any $B_{Total}$, the $B_{Free}$ and risk of BIND increase as $B_{Tmax}$ and $K_A$ decrease irrespective of the $B_{Total}$ as illustrated in FIG. 3 and FIG. 4, i.e. at any $B_{Total}$ there is more brain exposure to bilirubin and increased risk of, or presence of, hyperbilirubinemia and bilirubin toxicity, optionally bilirubin neurotoxicity, optionally BIND as $B_{Tmax}$ and $K_A$ decrease.

In alternative embodiments, provided are methods for quantifying how well (or how clinically efficiently) plasma, serum or blood binds bilirubin in an individual, comprising determining the maximum total bilirubin concentration ($B_{Tmax}$) and its corresponding equilibrium association constant ($K_A$) for comparison with the, optionally median $B_{Tmax}$ and $K_A$ for a comparable population. If R is the $B_{FreeStandard}$ obtained at a mandatory treatment $B_{Total}$ and optionally the median $B_{Tmax}$ and $K_A$ for the population, the patient's $B_{Total}$ at which R occurs $$= \frac{R \cdot K_A \cdot B_{Tmax}}{1 + (K_A \cdot R)}$$

wherein $B_{Tmax}$ and $K_A$ are the individual's $B_{Tmax}$ and $K_A$), wherein $$B_{Free} = \frac{B_{Total}}{K_A(B_{Tmsx} - B_{Total})}$$

and $B_{Total}$ are the concentrations of the non-albumin bound or free bilirubin and total bilirubin, respectively, and measuring $B_{Total}$ and $B_{Free}$ before and after enrichment of the sample with bilirubin to provide $B_{Total\_1}$, $B_{Free\_1}$ and $B_{Total\_2}$, $B_{Free\_2}$ to obtain two equations with two unknowns ($B_{Tmax}$ and $K_A$), that can be solved for $B_{Tmax}$ as shown below:

$$B_{Tmax} = \frac{B_{Total}B_{Total\_2}(B_{Free\_2} - B_{Free})}{B_{Total}B_{Free\_2} - B_{Total\_2}B_{Free}}$$

The calculated $B_{Tmax}$, $B_{Total}$, and $B_{Free}$ are then entered into $$B_{Free} = \frac{B_{Total}}{K_A(B_{Tmsx} - B_{Total})}$$

to obtain $$K_A = \frac{B_{Total}}{B_{Free}(B_{Tmsx} - B_{Total})},$$

or alternatively, $K_A$ is the negative intercept and $B_{Tmax}$ is the negative slope divided by the intercept of $$\frac{1}{B_{Free}}\ \text{versus}\ \frac{1}{B_{Total}}$$

as the reciprocal of $$B_{Free} = \frac{B_{Total}}{K_A(B_{Tmsx} - B_{Total})}$$

is the linear equation $$\frac{1}{B_{Free}} = \frac{B_{Tmax} \cdot K_A}{B_{Total}} - K_A,$$

wherein optionally enrichment comprises increasing the amount of bilirubin in the sample to approximately the is mandatory treatment $B_{Total}$, e.g., up to about 20 mg/dL in newborns less than (<) 35 weeks gestation (TABLE 1) and up to about 30 mg/dL in newborns greater than 35 or more weeks of gestation, see e.g., see Wickremasinghe A C, et al. Risk of sensorineural hearing loss and bilirubin exchange transfusion thresholds. Pediatrics 2015; 136: 505-512.
wherein optionally the method comprises:
(a) providing or taking a plasma, blood or serum sample from the individual;
(b) measuring $B_{Total}$ and $B_{Free}$ in the sample, and
(c) enriching the plasma, blood or serum sample with bilirubin (or, adding exogenous bilirubin to the sample).
wherein optionally enrichment comprises increasing the amount of bilirubin in the sample to approximately the concentration at which exchange transfusion is mandatory, e.g. up to about 20 mg/dL in newborns less (<) 35 weeks gestation (TABLE 1) and up to about 30 mg/dL in newborns greater than or equal to 35 weeks gestation,
(d) measuring $B_{Total}$ and $B_{Free}$ in the sample after bilirubin enrichment, and
(e) determining the maximum total bilirubin concentration ($B_{Tmax}$) and the corresponding equilibrium association constant ($K_A$),
wherein if the individual's $B_{Free}$ is above the $B_{FreeStandard}$ determined at a current treatment $B_{Total}$ (optionally the mandatory treatment $B_{Total}$ as set forth in Table 1, and optionally the mandatory $B_{Total}$ for exchange transfusion is 14 mg/dL for newborns less than (<) 28 weeks gestation) and optionally the median $B_{Tmax}$ and $K_A$ for the comparable population (and optionally the median $B_{Tmax}$ is 22.0 mg/dL and median $K_A$ is 1.16 µg/dL, and optionally $$B_{FreeStandard} = \frac{B_{Total}}{K_A(B_{Tmax} - B_{Total})} =$$

$$\frac{14 \text{ mg/dL}}{1.16 \text{ dL/µg} (22.0 \text{ mg/dL} - 14 \text{ mg/dL})} = 1.51 \text{ µg/dL},$$

see FIG. 4) irrespective of the individual's $B_{Total}$, this indicates that the plasma or serum is not clinically efficient in binding or retaining bilirubin and that treatment for hyperbilirubinemia (jaundice) is indicated.

and optionally the method further comprises assessing the need for treatment of hyperbilirubinemia in an individual at any $B_{Total}$ by quantifying bilirubin binding and comparing the individual's $B_{Tmax}$ and $K_A$ with, optionally, the median $B_{Tmax}$ and $K_A$ in the appropriate comparable newborn population (optionally the median $B_{Tmax}$=22.0 mg/dL and $K_A$=1.16 dL/µg for newborns less than (<) 28 weeks gestation as set forth in TABLE 2), wherein a $B_{Tmax}$ and $K_A$ in the patient that are lower than the median $B_{Tmax}$ and $K_A$ indicate more brain exposure to bilirubin at any $B_{Total}$ and more risk of bilirubin toxicity, optionally bilirubin neurotoxicity, optionally bilirubin-induced neurological dysfunction (BIND), and treatment of hyperbilirubinemia, including jaundice, at $B_{Total}$ below current treatment $B_{Total}$, e.g. Table 1, may be warranted, and optionally the method further comprises assessing the need for treatment of hyperbilirubinemia, including jaundice, in a patient at $$B_{Total} = \frac{B_{FreeStandard} \cdot K_A \cdot B_{Tmax}}{1 + (K_A \cdot B_{FreeStandard})}$$

unique for that individual at the patient's $B_{Tmax}$ and $K_A$ and wherein $B_{Total}$ may be different than a current treatment $B_{Total}$, e.g. Table 1, and $B_{FreeStandard}$ is the $B_{Free}$ at optionally the median $B_{Tmax}$ and $K_A$ for the patient's peers, optionally the population, at a current treatment $B_{Total}$ $$\left( B_{FreeStandard} = \frac{\text{Treatment } B_{Total}}{\text{median } K_A (\text{median } B_{Tmax} - \text{Treatment } B_{Total})} \right)$$

(optionally, if a patient is less than (<) 28 weeks gestation, the mandatory exchange transfusion is $B_{Total}$=14 mg/dL as shown in TABLE 1, and at the optionally median $B_{Tmax}$ of 22.0 mg/dL and median $K_A$ of 1.16 dL/µg, $$B_{FreeStandard} = \frac{14 \text{ mg/dL}}{1.16 \text{ dL/µg}(22.0 \text{ mg/dL} - 14 \text{ mg/dL})} = 1.51 \text{ µg/dL} \bigg);$$

and the relative risk of BIND at the individual's $$B_{Total} = \frac{B_{FreeStandard} \cdot K_A \cdot B_{Tmax}}{1 + (K_A \cdot B_{FreeStandard})}$$

would be the same as that occurring at the treatment $B_{Total}$ (Table 1) and optionally the median $B_{Tmax}$ and $K_A$ for the population and there is sufficient brain exposure to bilirubin and a risk of bilirubin toxicity, optionally bilirubin neurotoxicity, optionally bilirubin-induced neurological dysfunction (BIND), to warrant treatment for the hyperbilirubinemia, or jaundice.

In alternative embodiments, provided are methods for quantifying how well plasma, serum, or blood binds bilirubin, comprising determining the maximum total bilirubin concentration ($B_{Tmax}$) and the equilibrium association constant ($K_A$),
wherein $$B_{Free} = \frac{B_{Total}}{K_A(B_{Tmax} - B_{Total})},$$

and $B_{Free}$ and $B_{Total}$ are the concentrations of the non-albumin bound or free bilirubin and total bilirubin, respectively, and optionally the method determines whether bilirubin binding, i.e. $B_{Tmax}$ and $K_A$, is normal (e.g. $B_{Tmax}$ and $K_A$ at or above the median or average for comparable individuals), or below normal, by comparing the $B_{Tmax}$ and $K_A$ in a patient with optionally the average or median values in comparable individuals, wherein optionally the patient is a newborn infant, wherein lower than normal $B_{Tmax}$ and $K_A$ in the patient indicates that at $B_{Total}$ below current treatment $B_{Total}$ (e.g. Table 1) there is more brain exposure to bilirubin and more risk of, or the presence of, hyperbilirubinemia and bilirubin toxicity, optionally bilirubin neurotoxicity, optionally bilirubin-induced neurological dysfunction (BIND), and optionally the method further comprises assessing the need for hyperbilirubinemia (or jaundice) treatment by comparing the $B_{Free}$ with $B_{FreeStandard}$ for comparable individuals, optionally $B_{FreeStandard}$ determined at the treatment $B_{Total}$ and median $B_{Tmax}$ and $K_A$ for comparable individuals, wherein the patient is a newborn infant, wherein a $B_{Free}$ greater than or equal to $B_{FreeStandard}$ indicates sufficient brain exposure to bilirubin and risk of bilirubin toxicity, optionally bilirubin neurotoxicity, optionally bilirubin-induced neurological dysfunction (BIND), to warrant treatment for hyperbilirubinemia (e.g., jaundice), and optionally the method further comprises assessing the need for hyperbilirubinemia (including jaundice) treatment in a patient at a unique $B_{Total}$ below that at which current clinical practice deems treatment should be considered by determining the unique $B_{Total}$ at which the patient's $$B_{Total} = \frac{B_{FreeStandard} \cdot K_A \cdot B_{Tmax}}{1 + (K_A \cdot B_{FreeStandard})}$$

as determined using the patient's $B_{Tmax}$, and $K_A$ and the patient's peers, optionally population, $B_{FreeStandard}$ (e.g. if the patient is less than (<) 28 weeks gestation, $B_{FreeStandard}$ at the mandatory exchange transfusion $B_{Total}$ of 14 mg/dL (TABLE 1) and optionally the median $B_{Tmax}$ of 22.0 mg/dL and $K_A$ of 1.16 dL/µg (TABLE 2) is $$B_{FreeStandard} = \frac{\text{Treatment } B_{Total}}{\text{median } K_A(\text{median } B_{Tmax} - \text{Treatment } B_{Total})} =$$

$$\frac{14 \text{ mg/dL}}{1.16 \text{ dL/µg}(22.0 \text{ mg/dL} - 14 \text{ mg/dL})} 1.51 \text{ µg/dL},$$

and a newborn less than 28 weeks gestation with e.g. a $25^{th}$ percentile $B_{Tmax}$ of 14.3 mg/dL and $K_A$ of 0.75 dL/µg would reach the $B_{FreeStandard}$ of 1.51 µg/dL at $$B_{Total} = \frac{B_{FreeStandard} \cdot K_A \cdot B_{Tmax}}{1 + (K_A \cdot B_{FreeStandard})} = \frac{1.51 \frac{\mu g}{dL} \cdot 0.75 \frac{dL}{\mu g} 14.3 \frac{mg}{dL}}{1 + \left(0.75 \frac{dL}{\mu g} 1.51 \frac{\mu g}{dL}\right)} = 7.6 \text{ mg/dL},$$

about half of the current mandatory exchange transfusion $B_{Total}$ of 14 mg/dL for newborns less than (<) 28 weeks gestation per Table 1); and at the patient's unique $B_{Total}$, the brain exposure to bilirubin and of risk bilirubin toxicity, optionally bilirubin neurotoxicity, and optionally bilirubin-induced neurological dysfunction (BIND), is the same as that occurs at the current mandatory treatment $B_{Total}$, and treatment is warranted despite a patient's $B_{Total}$ below the mandatory treatment $B_{Total}$.

In alternative embodiments, provided are computer-implemented methods comprising a method as provided herein (e.g., a method as provided herein), or for executing a method as provided herein to determine a $B_{Total}$ and $K_A$, and optionally further comprising: receiving the data elements; and storing the data elements.

In alternative embodiments, provided are computer program products for processing data and determining a $B_{Tmax}$ and $K_A$ obtained by a novel method using $B_{Total}$ and $B_{Free}$ measured before and after bilirubin enrichment of a plasma sample, the computer program product comprising a computer-implemented method as provided herein.

In alternative embodiments, provided are Graphical User Interface (GUI) computer program products for determining $B_{Tmax}$ and $K_A$ obtained by a novel method using $B_{Total}$ and $B_{Free}$ measured before and after bilirubin enrichment of a plasma sample, comprising the computer-implemented method as provided herein.

In alternative embodiments, provided are computer systems comprising a processor and a data storage device wherein said data storage device has stored thereon: (a) a computer-implemented method as provided herein; (b) a computer program product as provided herein; (c) a Graphical User Interface (GUI) computer program product as provided herein; or, (d) a combination thereof.

In alternative embodiments, provided are non-transitory memory medium comprising program instructions for running, processing and/or implementing: (a) a computer-implemented method as provided herein; (b) a computer program product as provided herein; (c) a Graphical User Interface (GUI) computer program product as provided herein; or, (d) a combination thereof.

In alternative embodiments, provided are non-transitory computer readable medium storing a computer program product for inputting data and performing calculations for determining a $B_{Tmax}$ and $K_A$ obtained by a novel method using $B_{Total}$ and $B_{Free}$ measured before and after bilirubin enrichment of a plasma sample, comprising the computer-implemented method as provided herein.

In alternative embodiments, provided are non-transitory computer-readable storage medium comprising computer-readable instructions that, when executed by a processor of a computing device, cause the computing device to run, process and/or implement: (a) a computer-implemented method as provided herein; (b) a computer program product as provided herein; (c) a Graphical User Interface (GUI) computer program product as provided herein; or, (d) a combination thereof.

In alternative embodiments, provided are computer program products comprising: a non-transitory computer-readable storage medium; and program instructions residing in said storage medium which, when executed by a computer, run, process and/or implement: (a) a computer-implemented method as provided herein; (b) a computer program product as provided herein; (c) a Graphical User Interface (GUI) computer program product as provided herein; or, (d) a combination thereof.

In alternative embodiments, provided are computer program storage devices, embodied on a tangible computer readable medium, comprising: (a) a computer-implemented method as provided herein; (b) a computer program product as provided herein; (c) a Graphical User Interface (GUI) computer program product as provided herein; or, (d) a combination thereof.

In alternative embodiments, provided are computers or equivalent electronic systems, comprising: a memory; and a processor operatively coupled to the memory, the processor adapted to execute program code stored in the memory to: run, process and/or implement: (a) a computer-implemented method as provided herein; (b) a computer program product as provided herein, (c) a Graphical User Interface (GUI) computer program product as provided herein; or, (d) a combination thereof.

In alternative embodiments, provided are systems, comprising: a memory configured to: store values associated with a plurality of data points and/or a plurality of data elements, and a processor adapted to execute program code stored in the memory to: run, process and/or implement: (a) a computer-implemented method as provided herein; (b) a computer program product as provided herein; (c) a Graphical User Interface (GUI) computer program product as provided herein; or, (d) a combination thereof.

In alternative embodiments, provided are computer-implemented systems for providing an application access to an external data source or an external server process via a connection server, and providing the ability to store values associated with the plurality of data points and/or the plurality of data elements, and an application for running, processing and/or implementing: (a) a computer-implemented method as provided herein; (b) a computer program product as provided herein; (c) a Graphical User Interface (GUI) computer program product as provided herein; or, (d) a combination thereof.

In alternative embodiments, provided are devices, e.g., medical or analytical devices, capable of quantifying how well plasma binds bilirubin, wherein the device is capable of measuring $B_{Free}$ (non-albumin bound or free bilirubin concentration), and $B_{Total}$ (total bilirubin concentration), and communicating this data to a computer-implemented system as provided herein, a system as provided herein, or a computer or equivalent electronic system as provided herein, which can execute the computer-implemented method as provided herein, to determine or calculate, and output, e.g., to a user, a $B_{Tmax}$ and $K_A$ obtained by a novel method using $B_{Total}$ and $B_{Free}$ measured before and after bilirubin enrichment of a plasma sample, wherein optionally the computer-implemented system as provided herein, the system as provided herein, or the computer or equivalent electronic system as provided herein, is part of or within the device, or is remote to (e.g., only directly connected to or wirelessly connected to) the device, wherein the device comprises components, optionally robotic chemistry components, capable of measuring: total serum bilirubin concentration ($B_{Total}$); unbound bilirubin or free bilirubin concentration ($B_{Free}$) before and after bilirubin enrichment to obtain $B_{Tmax}$, and $K_A$ from a sample, optionally a plasma or a blood sample, wherein optionally the computer-implemented system, the system, or the computer or equivalent electronic system is an integral part of the device, or is operatively linked remotely to the device, wherein optionally the device comprises an automated micro-fluid handling technology, optionally a zone fluidics system or a robotic zone fluidics analytical system.

In alternative embodiments, provided are methods or processes, or systems or devices, for the diagnosis or prognosis of (or predicting the likelihood of acquiring):

the risk of bilirubin toxicity, optionally bilirubin neurotoxicity, optionally BIND, a bilirubin-induced neurodevelopmental impairment, or a neurodevelopmental impairment having toxic levels of bilirubin as a causative agent, optionally in a newborn, optionally comprising an encephalopathy or kernicterus, or sudden neurotoxicity (acute bilirubin encephalopathy), or choreoathetotic cerebral palsy, a bilirubin-induced hearing impairment, or a hearing impairment having toxic levels of bilirubin as a causative agent, a bilirubin-induced autism, or an autism having toxic levels of bilirubin as a causative agent, a bilirubin-induced high tone hearing loss, a bilirubin-induced paralysis of upward gaze, or a bilirubin-induced yellow staining of the teeth, in an individual in need thereof, comprising:

quantifying how well that individual's plasma binds bilirubin comprising:

(a) using a method as provided herein; or (b) determining the maximum total bilirubin concentration ($B_{Tmax}$) and the corresponding equilibrium association constant ($K_A$), wherein $$B_{Free} = \frac{B_{Total}}{K_A(B_{Tmsx} - B_{Total})},$$

and $B_{Free}$ and $B_{Total}$ are the concentrations of the non-albumin bound or free bilirubin and total bilirubin, respectively, wherein the method determines whether bilirubin binding is normal, or below normal, and the relative risk of BIND by comparing a $B_{Free}$ with $B_{FreeStandard}$ for the comparable population of peers (e.g. for newborns less than (<) 28 gestation per Table 1, at the mandatory exchange transfusion $B_{Total}$ of 14 mg/dL and optionally the median $B_{Tmax}$ of 22.0 mg/dL and $K_A$ of 1.16 dL/μg per Table 2, $$B_{FreeStandard} = \frac{\text{Treatment } B_{Total}}{\text{median } K_A(\text{median } B_{Tmax} - \text{Treatment } B_{Total})} =$$

$$\frac{14 \text{ mg/dL}}{1.16 \text{ } dL/\mu g(22.0 \text{ mg/}dL - 14 \text{ mg/}dL)} 1.51 \text{ } \mu g/dL$$

and a unique $B_{Total}$ at which $B_{FreeStandard}$ occur $$\left(B_{Total} = \frac{B_{FreeStandard} \cdot K_A \cdot B_{Tmax}}{1 + (K_A \cdot B_{FreeStandard})}\right)$$

with a current treatment $B_{Total}$ for the comparable population of peers (e.g. for newborns less than (<) 28 gestation with a mandatory exchange transfusion at $B_{Total}$ of 14 mg/dL per Table 1, a patient with a 25$^{th}$ percentile $B_{Tmax}$ (14.3 mg/dL) and $K_A$ (0.75 dL/μg) will reach the $B_{FreeStandard}$ of 1.51 μg/dL at $$B_{Total} =$$

$$\frac{B_{FreeStandard} \cdot K_A \cdot B_{Tmax}}{1 + (K_A \cdot B_{FreeStandard})} = \frac{1.51 \frac{\mu g}{dL} \cdot 0.75 \frac{dL}{\mu g} 14.3 \frac{\text{mg}}{dL}}{1 + \left(0.75 \frac{dL}{\mu g} 1.51 \frac{\mu g}{dL}\right)} = 7.6 \text{ mg/}dL),$$

wherein optionally the patient is a newborn, wherein if a $B_{Free}$ is equal to or greater than $B_{FreeStandard}$ or a $B_{Total}$ is less than a treatment $B_{Total}$, this indicates more brain exposure to bilirubin and increased risk of, or presence of, significant hyperbilirubinemia (including jaundice) or bilirubin toxicity, optionally bilirubin neurotoxicity, optionally BIND, a bilirubin-induced neurodevelopmental impairment, or a neurodevelopmental impairment having toxic levels of bilirubin as a causative agent, optionally in a newborn, optionally comprising an encephalopathy or kernicterus, or sudden neurotoxicity (acute bilirubin encephalopathy), or choreoathetotic cerebral palsy, a bilirubin-induced hearing impairment, or a hearing impairment having toxic levels of bilirubin as a causative agent, a bilirubin-induced autism, or an autism having toxic levels of bilirubin as a causative agent, a bilirubin-induced high tone hearing loss, a bilirubin-induced paralysis of upward gaze, or a bilirubin-induced yellow staining of the teeth.

In alternative embodiments, provided are methods for treating, ameliorating, reversing or preventing in an individual in need thereof (optionally a jaundiced newborn):

significant hyperbilirubinemia (including jaundice) or bilirubin toxicity, optionally bilirubin neurotoxicity, optionally BIND, a bilirubin-induced neurodevelopmental impairment, or a neurodevelopmental impairment having toxic levels of bilirubin as a causative agent, optionally in a newborn, optionally comprising an encephalopathy or kernicterus, or sudden neurotoxicity (acute bilirubin encephalopathy), or choreoathetotic cerebral palsy, a bilirubin-induced hearing impairment, or a hearing impairment having toxic levels of bilirubin as a causative agent, a bilirubin-induced autism, or an autism having toxic levels of bilirubin as a causative agent, a bilirubin-induced high tone hearing loss, a bilirubin-induced paralysis of upward gaze, or a bilirubin-induced yellow staining of the teeth.

the method comprising:

(a) using methods as provided herein or a device as provided herein to determine whether bilirubin binding is normal, or below normal, by comparing a $B_{Tmax}$ and $K_A$ in a patient versus optionally an average or median $B_{Tmax}$ and $K_A$ in a comparable newborn population and the $B_{Free}$ in a patient with a $B_{FreeStandard}$ in the comparable population and the $B_{Total}$ in a patient at which $B_{Free} = B_{FreeStandard}$, wherein if the individual in need thereof has a $B_{Free}$ equal to or greater $B_{FreeStandard}$ or $B_{Total}$ below a current treatment $B_{Total}$, this indicates more brain bilirubin exposure and more risk of, or the presence of:

significant hyperbilirubinemia (including jaundice) or bilirubin toxicity, optionally bilirubin neurotoxicity, optionally BIND, a bilirubin-induced neurodevelopmental impairment, or a neurodevelopmental impairment having toxic levels of bilirubin as a causative agent, optionally in a newborn, optionally comprising an encephalopathy or kernicterus, or sudden neurotoxicity (acute bilirubin encephalopathy), or choreoathetotic cerebral palsy, a bilirubin-induced hearing impairment, or a hearing impairment having toxic levels of bilirubin as a causative agent, a bilirubin-induced autism, or an autism having toxic levels of bilirubin as a causative agent, a bilirubin-induced high tone hearing loss, a bilirubin-induced paralysis of upward gaze, or a bilirubin-induced yellow staining of the teeth;

and (b) if the individual in need thereof has a $B_{Free}$ equal to or greater than $B_{FreeStandard}$ or a $B_{Total}$ below a current treatment $B_{Total}$, then treating (or commencing treatment for), ameliorating, reversing or preventing the individual in need thereof for:

significant hyperbilirubinemia (including jaundice) or bilirubin toxicity, optionally bilirubin neurotoxicity, optionally BIND, a bilirubin-induced neurodevelopmental impairment, or a neurodevelopmental impairment having toxic levels of bilirubin as a causative agent, optionally in a newborn, optionally comprising an encephalopathy or kernicterus, or sudden neurotoxicity (acute bilirubin encephalopathy), or choreoathetotic cerebral palsy, a bilirubin-induced hearing impairment, or a hearing impairment having toxic levels of bilirubin as a causative agent, a bilirubin-induced autism, or an autism having toxic levels of bilirubin as a causative agent, a bilirubin-induced high tone hearing loss, a bilirubin-induced paralysis of upward gaze, or a bilirubin-induced yellow staining of the teeth.

In alternative embodiments, provided are devices for use in:

treating, ameliorating, reversing or preventing the individual in need thereof for:

significant hyperbilirubinemia (including jaundice) or bilirubin toxicity, optionally bilirubin neurotoxicity, optionally BIND, a bilirubin-induced neurodevelopmental impairment, or a neurodevelopmental impairment having toxic levels of bilirubin as a causative agent, optionally in a newborn, optionally comprising an encephalopathy or kernicterus, or sudden neurotoxicity (acute bilirubin encephalopathy), or choreoathetotic cerebral palsy, a bilirubin-induced hearing impairment, or a hearing impairment having toxic levels of bilirubin as a causative agent, a bilirubin-induced autism, or an autism having toxic levels of bilirubin as a causative agent, a bilirubin-induced high tone hearing loss, a bilirubin-induced paralysis of upward gaze, or a bilirubin-induced yellow staining of the teeth.

wherein the device comprises a device as provided herein, a computer-implemented system as provided herein, a system as provided herein, or a computer or equivalent electronic system as provided herein, and the device can determine whether bilirubin binding is normal, or below normal, by using a novel method for measuring $B_{Total}$ and $B_{Free}$ before and after bilirubin enrichment of a sample to obtain and then compare a $B_{Tmax}$ and $K_A$ in a patient versus a $B_{Tmax}$ and $K_A$ in a comparable newborn population and $B_{Free}$ in the individual in need thereof versus a $B_{FreeStandard}$ in a comparable newborn population, wherein a higher than normal $B_{Free}$ or a $B_{FreeStandard}$ occurring in the individual in need thereof at a $B_{Total}$ below a current treatment $B_{Total}$ indicates more brain bilirubin exposure and more risk of, or the presence of:

significant hyperbilirubinemia (including jaundice) or bilirubin toxicity, optionally bilirubin neurotoxicity, optionally BIND, a bilirubin-induced neurodevelopmental impairment, or a neurodevelopmental impairment having toxic levels of bilirubin as a causative agent, optionally in a newborn, optionally comprising an encephalopathy or kernicterus, or sudden neurotoxicity (acute bilirubin encephalopathy), or choreoathetotic cerebral palsy, a bilirubin-induced hearing impairment, or a hearing impairment having toxic levels of bilirubin as a causative agent, a bilirubin-induced autism, or an autism having toxic levels of bilirubin as a causative agent, a bilirubin-induced high tone hearing loss, a bilirubin-induced paralysis of upward gaze, or a bilirubin-induced yellow staining of the teeth.

In alternative embodiments, provided are uses of device for:

treating, ameliorating, reversing or preventing the individual in need thereof for:

significant hyperbilirubinemia (including jaundice) or bilirubin toxicity, optionally bilirubin neurotoxicity, optionally BIND, a bilirubin-induced neurodevelopmental impairment, or a neurodevelopmental impairment having toxic levels of bilirubin as a causative agent, optionally in a newborn, optionally comprising an encephalopathy or kernicterus, or sudden neurotoxicity (acute bilirubin encephalopathy), or choreoathetotic cerebral palsy, a bilirubin-induced hearing impairment, or a hearing impairment having toxic levels of bilirubin as a causative agent, a bilirubin-induced autism, or an autism having toxic levels of bilirubin as a causative agent, a bilirubin-induced high tone hearing loss, a bilirubin-induced paralysis of upward gaze, or a bilirubin-induced yellow staining of the teeth, wherein the device comprises a device as provided herein, a computer-implemented system as provided herein, a system as provided herein, or a computer or equivalent electronic system as provided herein, and the device can determine whether bilirubin binding is normal, or below normal, by using a novel method for measuring $B_{Total}$ and $B_{Free}$ before and after bilirubin enrichment of a sample to obtain and then compare a $B_{Tmax}$ and $K_A$ in a patient versus optionally the average or median $B_{Tmax}$ and $K_A$ in a comparable newborn population and $B_{Free}$ in the individual in need thereof versus $B_{FreeStandard}$ in a comparable newborn population, wherein a lower than normal $B_{Tmax}$ and $K_A$ and $B_{Free}$ equal to or greater than $B_{FreeStandard}$ in the individual in need thereof indicates more brain bilirubin exposure and more risk of, or the presence of:

significant hyperbilirubinemia (including jaundice) or bilirubin toxicity, optionally bilirubin neurotoxicity, optionally BIND, a bilirubin-induced neurodevelopmental impairment, or a neurodevelopmental impairment having toxic levels of bilirubin as a causative agent, optionally in a newborn, optionally comprising an encephalopathy or kemicterus, or sudden neurotoxicity (acute bilirubin encephalopathy), or choreoathetotic cerebral palsy, a bilirubin-induced hearing impairment, or a hearing impairment having toxic levels of bilirubin as a causative agent, a bilirubin-induced autism, or an autism having toxic levels of bilirubin as a causative agent, a bilirubin-induced high tone hearing loss, a bilirubin-induced paralysis of upward gaze, or a bilirubin-induced yellow staining of the teeth.

The Bilirubin Binding Panel (BBP) described herein uses a novel panel of plasma laboratory tests (total bilirubin concentration, $B_{Total}$, and unbound or free bilirubin concentration, $B_{Free}$ measured before and after enrichment of a plasma sample with bilirubin) to calculate $B_{Tmax}$ and $K_A$ to provide clinicians with the $B_{Tmax} K_A$ that quantify a patient's bilirubin binding and the $B_{Free}$ that quantifies the relative risk of bilirubin-induced neurological dysfunction or BIND at that $B_{Total}$. These data are obtained by modifying the current method for measuring bilirubin binding such that $B_{Total}$ and $B_{Free}$ are measured before and after sample enrichment with bilirubin. This would require significantly more sample using standard methods (typically 25 µL of plasma) (see, e.g., see Ahlfors C E, et al. Measurement of unbound bilirubin by the peroxidase test using Zone Fluidics. Clin Chim Acta 2006; 365: 78-85), but Zone Fluidics/SIA analysis requires very small samples and can be adapted to performing the additional measurements using minimal increases in sample volume (less than 25 µL of plasma). Currently, clinicians have only $B_{Total}$ to assess the risk of BIND, and adding $B_{Free}$, $B_{Tmax}$, and $K_A$ to quantify binding assess the risk of BIND individualizes patient care and improves the determination of when and how to treat newborns with hyperbilirubinemia.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

The following drawings are illustrative of aspects of the invention and are not meant to limit the scope of the embodiments as encompassed by the claims.

or assuming $B_{Tmax}$=$A_{Total}$=26.4 mg/dL and $$K_A = \frac{8.3 \text{ mg}/dL}{0.51 \text{ µg}/dL(26.4 \text{ mg}/dL - 8.3 \text{ mg}/dL)} = 0.90 \text{ } dL/µg \text{ and}$$

$$B_{Free} = \frac{B_{Total}}{K_A(B_{Tmsx} - B_{Total})}(\diamond).$$

The $B_{Free}$ calculated using the single site albumin model deviate significantly from the measured $B_{Free}$ compared with $B_{Free}$ calculated using the paired data $B_{Tmax}$ and $K_A$.

Figure 1:
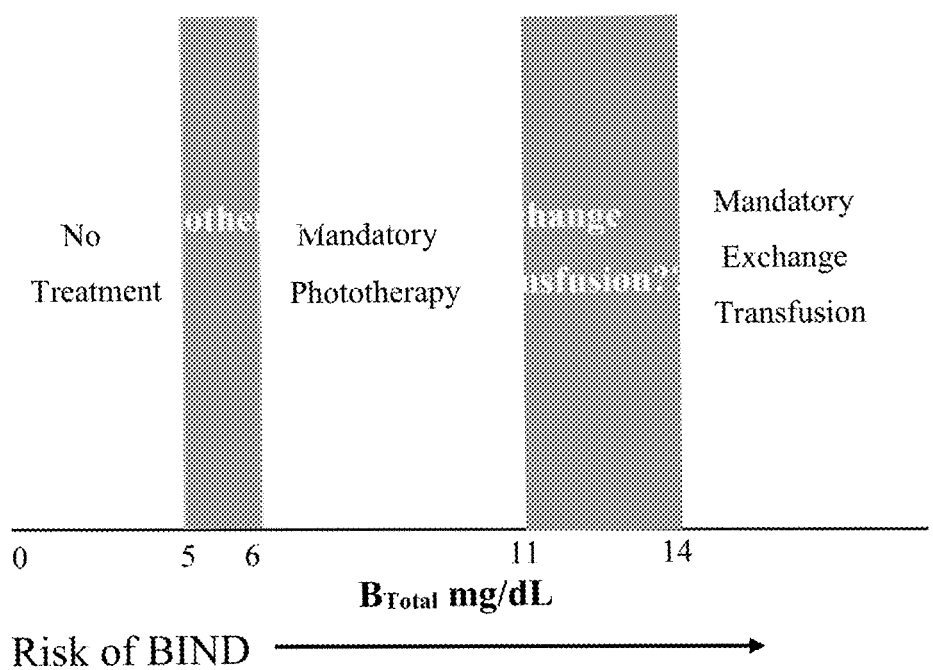
FIG. 1 illustrates current $B_{Total}$ treatment guidelines for newborns less than (<) 28 weeks gestation per TABLE 1. The risk of bilirubin-induced neurological dysfunction (BIND) at any $B_{Total}$ is unknown but increases as $B_{Total}$ increases. Phototherapy is considered at $B_{Total}$=5 mg/dL but not mandatory until it reaches 6 mg/dL and exchange transfusion is considered at $B_{Total}$=11 mg/dL but not mandatory until it reaches 14 mg/dL. The gray zones indicate considerable uncertainty and it is unclear how clinicians determine whether the risk of BIND is sufficient to warrant treatment at $B_{Total}$ in the gray zones. For example, how does a clinician decide whether a newborn with a $B_{Total}$=12 mg/dL needs an exchange transfusion?
Figure 2:
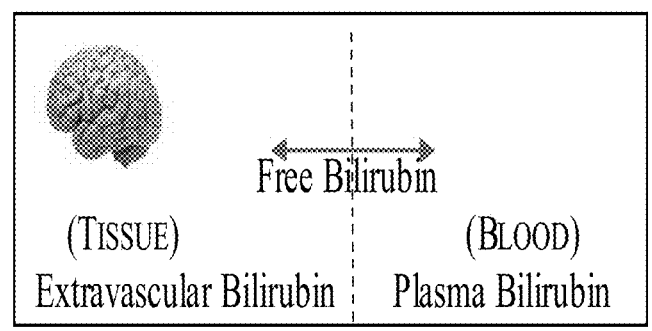
FIG. 2 schematically illustrates that the non-albumin bound or free bilirubin concentration ($B_{Free}$) governs the movement of bilirubin between tissues (brain) and blood. A baby with poor plasma bilirubin binding (higher $B_{Free}$ at any total bilirubin concentration) requires more accumulated bilirubin to reach a given $B_{Total}$ and will have, therefore, higher tissue levels of and brain exposure to bilirubin at that $B_{Total}$ relative to a patient with normal bilirubin binding that reaches that $B_{Total}$. Therefore the risk of BIND at any $B_{Total}$ is greater in a newborn with poor bilirubin binding.
Figure 3:
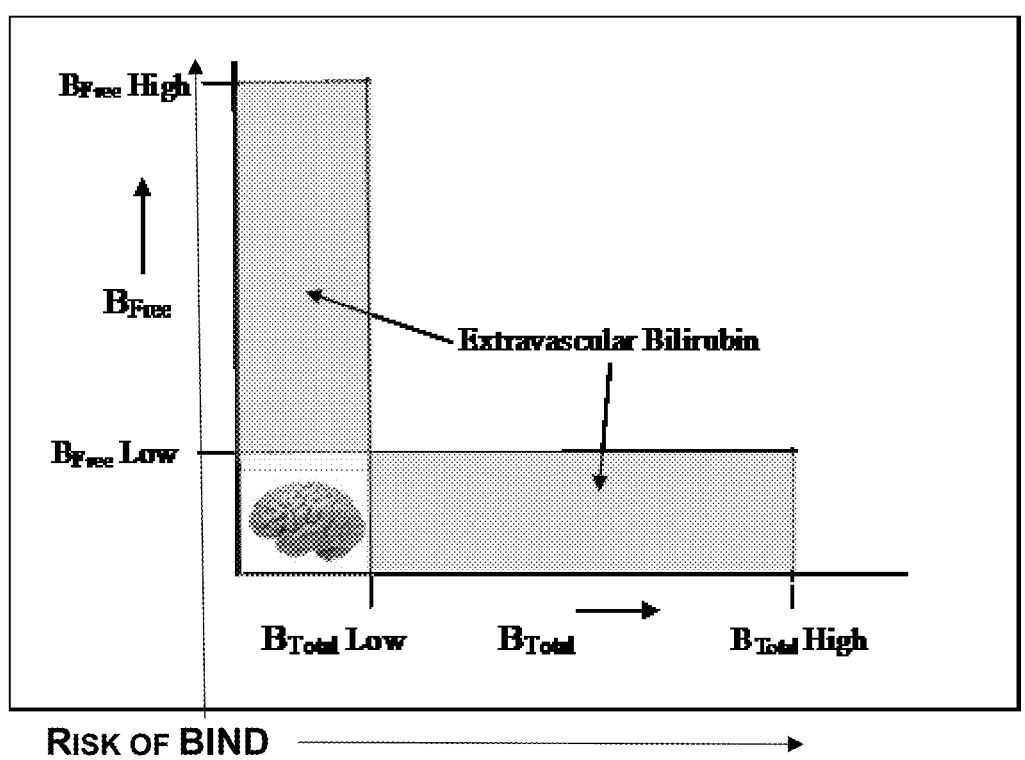
FIG. 3 illustrates that the risk of BIND increases as both $B_{Total}$ and $B_{Free}$ increase, and knowing both improves the assessment of risk as compared FIG. 1 wherein only $B_{Total}$ is used to assess risk.
Figure 4:
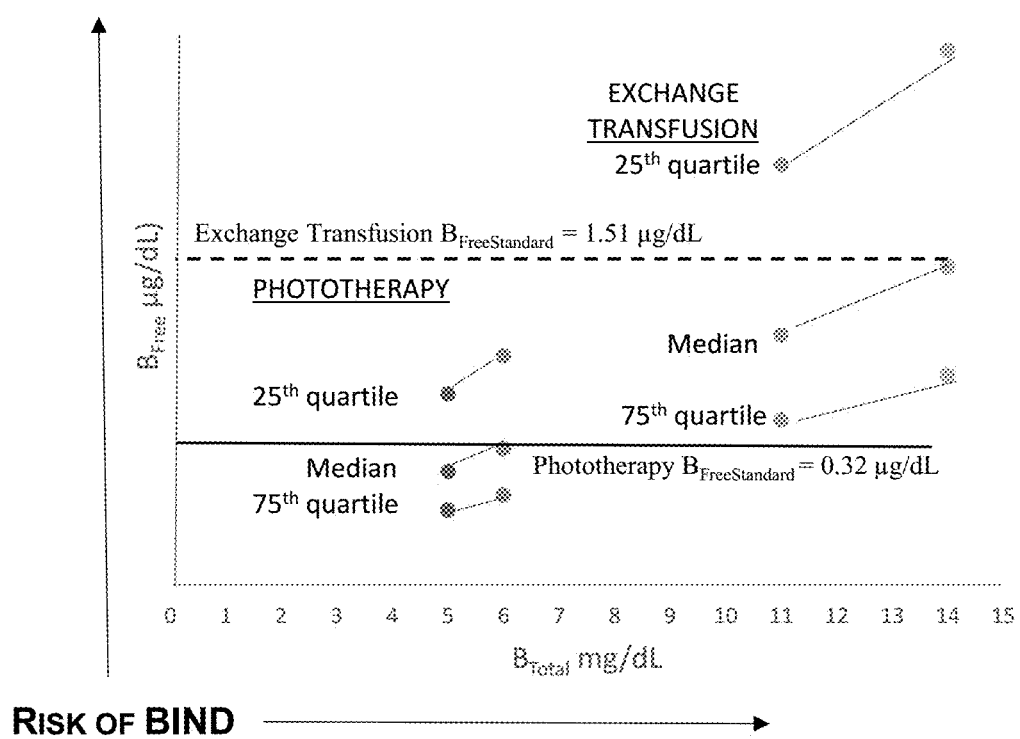
FIG. 4 illustrates the increase in $B_{Free}$ across the gray zones of FIG. 1 (blue dots to orange dots) that would occur at the median, 25$^{th}$, and 75$^h$ percentiles for a population and shows the $B_{FreeStandard}$ that occur at the mandatory phototherapy (0.32 µg/dL) and exchange transfusion (1.51 µg/dL) $B_{Total}$ of 6 mg/dL and 14 mg/dL, respectively, per Table 1 and median $B_{Tmax}$ (22.0 mg/dL) and $K_A$ (1.16 µg/dL) per Table 2 calculated using $$B_{FreeStandard} = \frac{\text{Treatment } B_{Total}}{\text{median } K_A(\text{median } B_{Tmax} - \text{Treatment } B_{Total})}.$$
Figure 6:
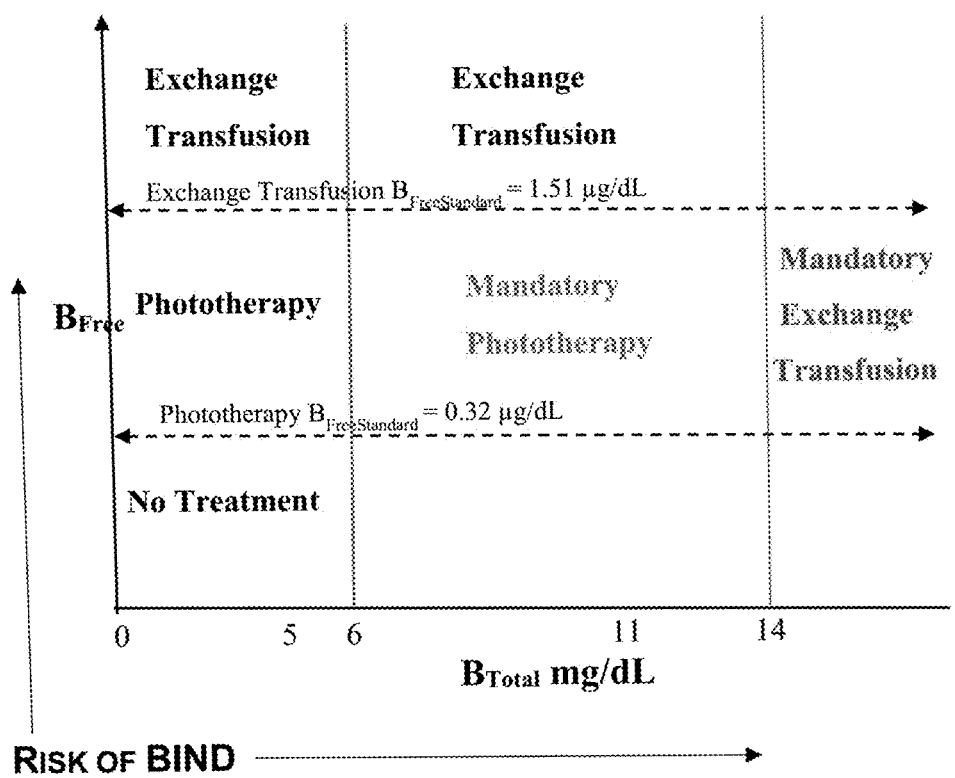

FIG. 6 illustrates the current treatment guidelines for newborns <28 weeks gestation shown in FIG. 1 modified using bilirubin binding, specifically the $B_{FreeStandard}$ obtained using the mandatory $B_{Total}$ phototherapy (6 mg/dL) and exchange transfusion (14 mg/dL) and median $B_{Tmax}$ (22.0 mg/dL) and $K_A$ (1.16 dL/µg) for the population of 31 newborns <28 weeks gestation in TABLE 2

$$B_{FreeStandard} = \frac{\text{Treatment } B_{Total}}{\text{median } K_A(\text{median } B_{Tmax} - \text{Treatment } B_{Total})}.$$

This eliminates the $B_{Total}$ gray zones where treatment is considered discretionary (uncertain) in FIG. 1.

Figure 7:
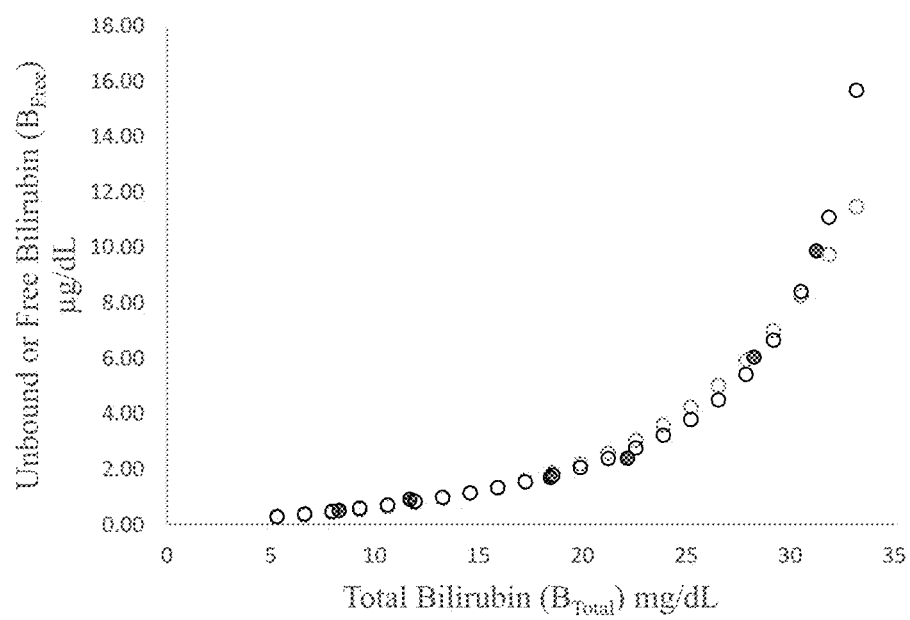

FIG. 7 illustrates measured $B_{Free}$ from TABLE 2 (●) versus $B_{Total}$; also shown are $B_{Free}$ calculated at 1 mg/dL increments in $B_{Total}$ using either the stoichiometric model using the equation $$B_{Free} = \frac{\left(-K_1(MR-1) \pm \sqrt{K_1(MR-1)^2 - 4(K_1K_2MR(MR-2))}\right)}{2K_1K_2(MR-2)}$$

where MR is the $B_{Total}$/Atotal molar ratio (TABLE 3) and $K_1$ (0.93 dL/μg) and $K_2$ (0.04 dL/μg) are the best-fit on-linear regression equilibrium constants to the stoichiometric mass action equation $$MR = \frac{K_1 B_{Free} + 2K_1 K_2 B_{Free}^2}{1 + K_1 B_{Free} + K_1 K_2 B_{Free}^2} \text{ or } B_{Free} = \frac{B_{Total}}{K_A(B_{Tmsx} - B_{Total})}$$

using $B_{Tmax}$=36.9 and $K_A$=0.57 dL/μg determined by pairing the binding data at $B_{Total}$=8.3 and 31.3 mg/dL (TABLE 3). The novel method for quantifying bilirubin binding described herein compares extremely well with the standard stoichiometric method.

Figure 8:
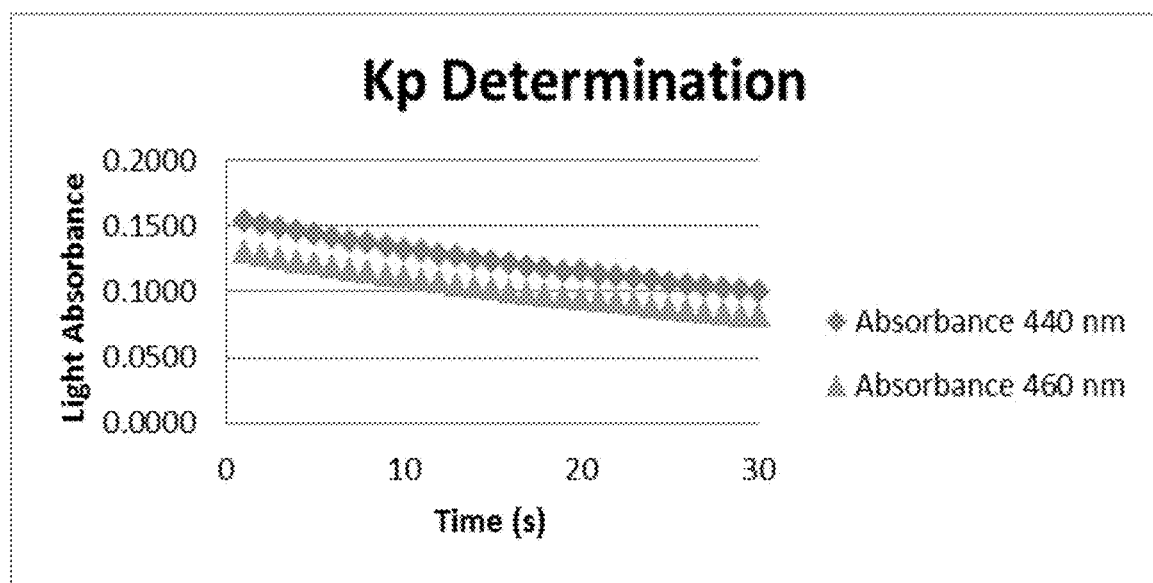

FIG. 8 illustrates that the Kp for the horseradish peroxidase catalyzed oxidation of bilirubin by peroxide is determine in bilirubin solutions containing no albumin (i.e. the total bilirubin concentration is equal to the unbound or free bilirubin concentration. Since the total bilirubin concentration is the absorbance at 440 nm divided by the extinction coefficient, the Kp is determined by integrating the velocity equation $$-\frac{dAbsorbance\ 440\ nm}{dt} = K_p \cdot HRP.$$

Absorbance 440 nm.

Figure 9:
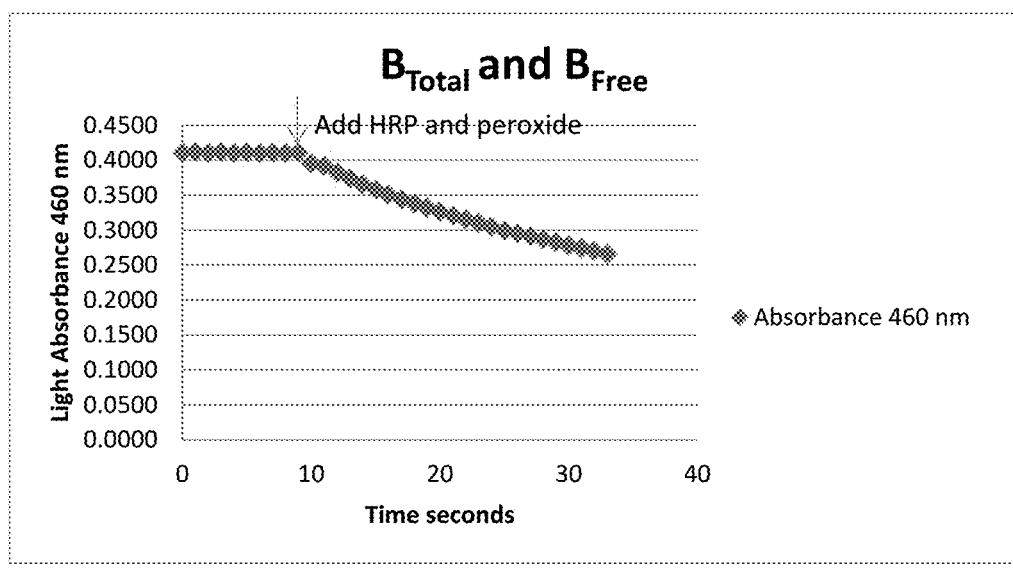

FIG. 9 illustrates the light absorbance at 460 nm of a bilirubin/albumin solution as a function of time before and after adding horseradish peroxidase (HRP) and peroxide. The initial absorbance at 460 nm is used to obtain $B_{Total}$ and the change in absorbance after adding HRP and peroxide is used to obtain the $B_{Free}$.

Like reference symbols in the various drawings indicate like elements.

DETAILED DESCRIPTION

In alternative embodiments, provided are methods, devices and multiplexed systems for assessing whether bilirubin binding is normal in a patient, e.g., a newborn infant, at and risk of bilirubin-induced neurological dysfunction (BIND), and whether the patient has plasma levels of bilirubin requiring treatment, and for diagnosing significant hyperbilirubinemia with increased risk of bilirubin neurotoxicity, including acute bilirubin encephalopathy and BIND. In alternative embodiments, provided are methods for treating or ameliorating, or preventing, the effects of in vivo toxic levels of bilirubin, or treating or ameliorating, or preventing bilirubin-induced neurological dysfunction (BIND), in individuals identified by methods as provided herein.

In alternative embodiments, provided are methods, which can be computer-implemented methods, for converting clinical laboratory data contained in a plasma bilirubin binding panel including: total serum bilirubin concentration ($B_{Total}$) and unbound bilirubin or free bilirubin concentration ($B_{Free}$) measured before and after bilirubin enrichment to calculate the clinically relevant maximum total bilirubin concentration $B_{Tmax}$ and its corresponding equilibrium association constant ($K_A$) outputting the $B_{Tmax}$ and $K_A$ to quantify how well a patient binds bilirubin and $B_{Free}$ and $B_{Total}$ at which the $B_{FreeStandard}$ for the population occurs to determine whether the risk of BIND is high enough to warrant treatment.

In alternative embodiments, also provided are analytical devices comprising automated micro-fluid handling technologies such as zone fluidics systems, for measuring: total serum bilirubin concentration ($B_{Total}$) and unbound bilirubin or free bilirubin concentration ($B_{Free}$) from a plasma, serum or blood sample before and after bilirubin enrichment, and also incorporating computer-implemented methods as provided herein to analyze this data and output a bilirubin binding panel including $B_{Total}$ and $B_{Free}$ measured before and after bilirubin enrichment, the clinically relevant maximum total bilirubin ($B_{Tmax}$) and its corresponding equilibrium association constant ($K_A$) to compare with $B_{Tmax}$ and $K_A$ in comparable individuals to accurately determine whether bilirubin binding is normal in a patient, and the clinically relevant diagnostics $B_{Free}$ and $B_{Total}$ at which $B_{FreeStandard}$ occurs, which when compared to the $B_{FreeStandard}$ in comparable individuals and the current treatment $B_{Total}$, respectively, accurately determine the risk of bilirubin-induced neurological dysfunction (BIND). In alternative embodiments, the computer or processor capacity to execute computer-implemented methods as provided herein for analyzing the measured clinical data is built within the device. In other embodiments, provided are systems where the computer or processor capacity to execute computer-implemented methods as provided herein is remote to the device, e.g., a zone fluidics analytical device.

In alternative embodiments, provided are methods, devices and multiplexed systems for assessing whether bilirubin binding is normal in a patient, for example, a newborn infant for the purpose of accurately assessing the presence or risk of acquiring bilirubin-induced neurological dysfunction (BIND) in that patient. The clinical use of bilirubin binding depends on measuring bilirubin binding and knowing the bilirubin binding parameters of the comparable population of newborns (e.g., well term newborns, newborns of the same gestational age as shown in Table 1, etc.). These data answer the questions: (1) "Is bilirubin binding normal in a newborn with hyperbilirubinemia?", and (2) "What is the risk of bilirubin-induced neurological dysfunction (BIND)?". For example, if the normal $B_{Tmax}$ and $K_A$ for the population is optionally the median $B_{Tmax}$ and $K_A$, a newborn with $B_{Tmax}$ and $K_A$ at the 25$^{th}$ percentile has poor bilirubin binding relative to the population (75% of the population have higher $B_{Tmax}$ and $K_A$ than the patient). At a mandatory treatment $B_{Total}$, e.g. per Table 1, wherein exchange transfusion is mandatory at $B_{Total}$=14 mg/dL for newborns less than (<) 28 weeks gestational age, the $B_{Free}$ at the Table 2 median $B_{Tmax}$ (22.0 mg/dL) and $K_A$ (1.16 dL/μg) is $$B_{Free} = \frac{B_{Total}}{K_A(B_{Tmsx} - B_{Total})} = \frac{14\ mg/dL}{1.16\ dL/\mu g\ (22.0\ mg/dL - 14\ mg/dL)} = 1.51\ \mu g/dL$$

and at the 25th percentile $B_{Tmax}$ (14.3 mg/dL) and $K_A$ (0.75 dL/μg)

$$B_{Free} = \frac{B_{Total}}{K_A(B_{Tmsx} - B_{Total})} = \frac{B_{Total}}{K_A(B_{Tmsx} - B_{Total})} = 62.2$$

μg/dL, with much higher risk of BIND. Therefore, determining $B_{Total}$, $B_{Free}$, $B_{Tmax}$ and $K_A$ in an individual in need thereof, optionally a newborn infant, quantify how well a newborn binds bilirubin and by comparing these metrics with those in a population of peers, it is possible to determine whether the risk of BIND is increased in the individual in need thereof. Obtaining the comparative population $B_{Tmax}$ and $K_A$ norms (e.g. mean, SD, range, median, quartiles, etc.) requires measuring them in an appropriate number of comparable newborns, typically about 400 patients, see e.g., Lott J A, et al. Estimation of reference ranges: how many subjects are needed? Clin Chem 1992; 38:648-650), and the $B_{Free}$, $B_{Tmax}$ and $K_A$ in a sample from an individual in need thereof quantify the risk of bilirubin-induced neurological dysfunction (BIND) at the $B_{Total}$ of the individual in need thereof and determine whether treatment is needed in the individual in need thereof at a $B_{Total}$ below that at which treatment is currently recommended for the population.

In alternative embodiments, the components of the bilirubin binding panel (BBP) including the measured $B_{Total}$ and $B_{Free}$ before and after bilirubin enrichment of the sample and the calculated clinically relevant $B_{Tmax}$ and its corresponding equilibrium association constant ($K_A$) are used to determine whether bilirubin binding is normal by comparing $B_{Tmax}$ and $K_A$ with optionally the median $B_{Tmax}$ and $K_A$ for the comparable population, and whether the risk of BIND is increased by comparing $B_{Free}$ with $B_{FreeStandard}$ as determined for the population at a current treatment $B_{Total}$ and optionally the median $B_{Tmax}$ and $K_A$ for the population. Additionally, the actual $B_{Total}$ at which treatment is needed can be determined using $B_{FreeStandard}$ and the $B_{Tmax}$ and $K_A$. The BBP as provided herein robustly quantifies bilirubin binding and can be used to determine whether bilirubin binding is normal when assessing the need for treatment of hyperbilirubinemia, including jaundice. The BBP can also be used as a screening test to determine the actual $B_{Total}$ at which the $B_{FreeStandard}$ and at which treatment may be warranted (e.g. if $B_{FreeStandard}$ for exchange transfusion is 1.51 μg/dL for newborns (<) 28 weeks per TABLES 1 and 2, a newborn in this group with a $B_{Total}$ of 3.0 mg/dL, a $B_{Free}$ of 0.18, a $B_{Tmax}$ of 20 mg/dL, and a $K_A$ of 1.00 dL/μg would reach the $B_{FreeStandard}$ at $$B_{Total} = \frac{B_{FreeStandard} \cdot K_A \cdot B_{Tmax}}{1 + (K_A \cdot B_{FreeStandard})} = \frac{1.51 \frac{\mu g}{dL} \cdot 1.00 \frac{dL}{\mu g} \cdot 20.0 \frac{mg}{dL}}{1 + \left(1.00 \frac{dL}{\mu g} \cdot 1.51 \frac{\mu g}{dL}\right)} = 12.0 \text{ mg/dL},$$

below the mandatory $B_{Total}$ exchange transfusion of 14 mg/dL). The Bilirubin Binding Panel as determined by methods provided herein, includes and assists rather than competes with $B_{Total}$ in determining the need for treatment.

In alternative embodiments, provided are methods and systems overcome difficulties in quantifying bilirubin binding using a simple technique that robustly quantifies bilirubin binding over the clinically relevant range of $B_{Total}$, e.g. $B_{Total}$ less than 20 mg/dL for newborns less than (<) 35 weeks gestation (see TABLE 1). In this approach, $B_{Tmax}$ is not $B_{Total}$ at which the all the plasma binding sites are occupied with bilirubin but instead the upper limit $B_{Total}$ of the functioning bilirubin binding sites within the clinically relevant range of $B_{Total}$, and $K_A$ is the corresponding composite of the $K_1 \ldots K_n$ equilibrium association constants. The chemical equilibrium is:

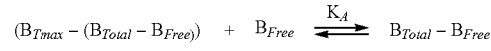

$$(B_{Tmax} - (B_{Total} - B_{Free})) + B_{Free} \underset{}{\overset{K_A}{\rightleftharpoons}} B_{Total} - B_{Free}$$

and since $B_{Free}$ is orders of magnitude less than $B_{Total}$ at clinically relevant $B_{Total}$, $B_{Total} - B_{Free} \cong B_{Total}$, the resulting mass action equations are shown below, $$B_{Free} = \frac{B_{Total} - B_{Free}}{K_A(B_{Tmax} - (B_{Total} - B_{Free}))} \cong \frac{B_{Total}}{K_A(B_{Tmax} - B_{Total})} \cdot B_{Free} = \frac{B_{Total}}{K_A(B_{Tmax} - B_{Total})}$$

can be readily solved by for $B_{Tmax}$ and $K_A$ by measuring $B_{Total}$ and $B_{Free}$ before and after enrichment of the sample with bilirubin to provide $B_{Total}$, $B_{Free}$, and $B_{Total\_2}$, $B_{Free\_2}$. These provide two equations with two unknowns ($B_{Tmax}$ and $K_A$), that can be solved for $B_{Tmax}$ as shown below:

$$B_{Tmax} = \frac{B_{Total} B_{Total\_2}(B_{Free\_2} - B_{Free})}{B_{Total} B_{Free\_2} - B_{Total\_2} B_{Free}}$$

The calculated $B_{Tmax}$, $B_{Total}$, and $B_{Free}$ are then entered into $$B_{Free} = \frac{B_{Total}}{K_A(B_{Tmsx} - B_{Total})}$$

to obtain $K_A$ $$K_A\left(K_A = \frac{B_{Total}}{B_{Free}(B_{Tmsx} - B_{Total})}\right),$$

or alternatively, $K_A$ is the negative intercept and $B_{Tmax}$ is the negative slope divided by the intercept of $$\frac{1}{B_{Free}} \text{ versus } \frac{1}{B_{Total}}$$

as the reciprocal of $$B_{Free} = \frac{B_{Total}}{K_A(B_{Tmsx} - B_{Total})}$$

is the linear equation $$\frac{1}{B_{Free}} = \frac{B_{Tmax} \cdot K_A}{B_{Total}} - K_A.$$

Figure 5:
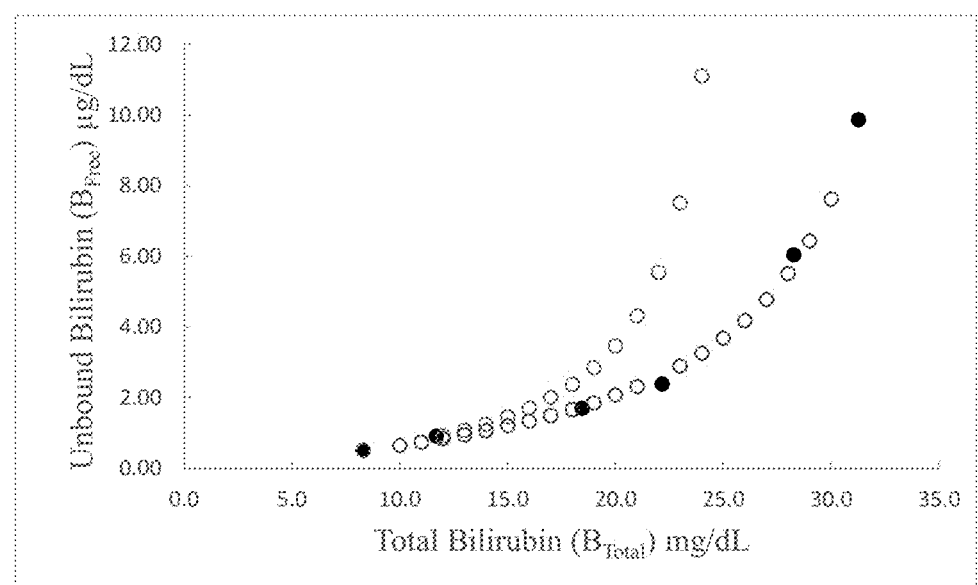
FIG. 5 plots the measured $B_{Free}$ from TABLE 3 (●) versus $B_{Total}$. Also shown are $B_{Free}$ calculated at 1 mg/dL increments in $B_{Total}$ using either $B_{Tmax}$=36.9 and $K_A$=0.57 dL/µg from the pairing data at $B_{Total}$=8.3 and 31.3 mg/dL where $$B_{Free} = \frac{B_{Total}}{K_A(B_{Tmsx} - B_{Total})}(\diamond)$$

TABLE 3 shows a bilirubin binding isotherm obtained in artificial serum containing bilirubin and with a human defatted albumin concentration ($A_{Total}$) of 3.0 g/dL. FIG. 5 illustrates the change in $B_{Free}$ (black dots) as $B_{Total}$ increases. The negative intercept of $1/B_{Free}$ versus $1/B_{Total}$, i.e. $K_A$, is 0.53 µg/dL and the negative slope/intercept, i.e. $B_{Tmax}$, is 37.5 mg/dL. The $B_{Tmax}$ and $K_A$ in Table 3 are calculated as described above using the lowest $B_{Total}$ (8.3 mg/dL) and $B_{Free}$ (0.51 µg/dL) paired with each of the other five measures of $B_{Total}$ and $B_{Free}$. The mean $B_{Tmax}$ and $K_A$ of all 15 possible pairings in TABLE 4 are 39.1 mg/dL and 0.56 dL/µg, respectively. The $B_{Free}$ calculated over 1 mg/dL increases in $B_{Total}$ using the $B_{Tmax}$ (36.9 mg/dL) and $K_A$ (0.57 dL/µg) obtained from pairing $B_{Total}$=8.3 mg/dL and $B_{Total}$=31.3 mg/dL overlap the measured binding points illustrated by the open orange circles in FIG. 5, but if $B_{Tmax}$=is assumed to be $A_{Total}$=26.4 mg/dL, and $$K_A = \frac{B_{Total}}{B_{Free}(B_{Tmax} - B_{Total})} =$$

$$\frac{8.3 \text{ mg/dL}}{0.51 \text{ µg/dL}(26.4 \text{ mg/dL} - 8.3 \text{ mg/dL})} = 0.90 \text{ dL/µg},$$

the calculated $B_{Free}$ deviate deviated significantly from the measured binding points as illustrated by the open blue circles in FIG. 5. This suggests $B_{Tmax}$ and the albumin concentration are not closely related, and plasma bilirubin binding sites are closely related to even though bilirubin is known to bind primarily to plasma albumin, and $B_{Tmax}$ and $A_{Total}$ in the 31 newborns less than 28 weeks gestation did not correlate significantly ($r^2$=0.02).

TABLE 3

| $B_{Total}/A_{Total}$ Molar Ratio | $B_{Total}$ mg/dL | $B_{Free}$ µg/dL | $B_{Tmax}$ mg/dL | $K_A$ dL/µg |
|---|---|---|---|---|
| 0.31 | 8.3 | 0.51 | | |
| 0.44 | 11.7 | 0.92 | 24.3 | 1.01 |
| 0.69 | 18.5 | 1.70 | 39.1 | 0.53 |
| 0.83 | 22.2 | 2.39 | 40.8 | 0.50 |
| 1.06 | 28.3 | 6.05 | 36.4 | 0.58 |
| 1.18 | 31.3 | 9.88 | 36.9 | 0.57 |

Quantifying bilirubin binding by determining $B_{Tmax}$ and $K_A$ in a population of newborns can be used to reduce the uncertainties in the current $B_{Total}$ guidelines for treatment (e.g. TABLE 1, FIG. 1). TABLE 2 summarizes binding data from 31 newborns less than (<) 28 weeks gestation, and knowing, e.g. the median, optionally the mean or average $B_{Tmax}$ and $K_A$ of a population, then a standard $B_{Free}$, i.e. $B_{FreeStandard}$ can be designated at a current treatment $B_{Total}$ (e.g. TABLE 1) and, e.g. the $B_{FreeStandard}$ at the median $B_{Tmax}$ and $K_A$ of the population is:

$$B_{FreeStandard} = \frac{\text{Treatment } B_{Total}}{\text{median } K_A(\text{median } B_{Tmax} - \text{Treatment } B_{Total})}$$

wherein, all else being comparable, half the population has a lower and half a higher risk of BIND versus the (usually unknown) risk of BIND at $B_{FreeStandard}$. For the half at greater risk of BIND $B_{FreeStandard}$ occurs at a $B_{Total}$ below the treatment $B_{Total}$, i.e. at the individual's $B_{Total}$, $B_{Tmax}$, and $K_A$ where $$B_{FreeStandard} = \frac{B_{Total}}{K_A(B_{Tmax} - B_{Total})}.$$

The risk of BIND in an individual is the same as that for the population at $B_{FreeStandard}$ when the individual's measured $B_{Free}$ is equal to or greater $B_{FreeStandard}$ or when the individual's $B_{Total}$ is equal to $$\frac{B_{FreeStandard} \cdot K_A \cdot B_{Tmax}}{1 + (K_A \cdot B_{FreeStandard})}$$

calculated using the patient's $B_{Tmax}$, and $K_A$ as the tissue levels of bilirubin, brain bilirubin exposure, and risk of BIND will be similar irrespective of the $B_{Total}$.

Novel methods for using measured serum or plasma $B_{Total}$ and $B_{Free}$ to obtain $B_{Tmax}$ and $K_A$ are provided herein as are their use to quantify bilirubin binding and assess the risk of BIND within the context of and reducing the uncertainties of current $B_{Total}$ guidelines for treatment of newborn hyperbilirubinemia as illustrated in FIG. 6 compared with FIG. 1. These data ($B_{Total}$, $B_{Free}$, $B_{Tmax}$, and $K_A$) comprise a Bilirubin Binding Panel (BBP) (see Ahlfors C E. The Bilirubin Binding Panel: A Henderson-Hasselbalch approach to neonatal hyperbilirubinemia. Pediatrics 2016; 138: e20154378) that will significantly reduce the uncertainties inherent in current treatment guidelines that use $B_{Total}$ only.

Quantifying Plasma Bilirubin Binding:

Defining normal bilirubin binding requires determining (1) how much bilirubin can be bound, and (2) how "tightly" bilirubin is bound. Since bilirubin binds mostly to plasma albumin, the concentration of albumin ($A_{Total}$) has long been used to estimate how much bilirubin can be bound, usually assuming that one albumin molecule binds one bilirubin molecule. However, albumin molecules can bind more than one bilirubin molecule and $A_{Total}$ per se is not a clinically useful estimate of how much bilirubin can be bound (i.e. $B_{Tmax}$).

Since each albumin molecule binds at least two bilirubin molecules over the clinically relevant range $B_{Total}$ encountered in newborns with hyperbilirubinemia (see FIG. 5), graphic analysis has often been used to quantify bilirubin binding (e.g. Jacobsen J. Binding of bilirubin to human serum albumin—Determination of the Dissociation Constants. FEBS Lett 1969; 5: 112-114), or alternatively nonlinear regression analysis of the polynomial mass action equations associated with multiple site binding are used (e.g. see Honoré B, Brodersen R. Albumin binding of anti-inflammatory drugs. Utility of a site-oriented versus a stoichiometric analysis. Mol Pharmacol 1984; 25: 137-150 and Klotz I M, Hunston D L. Protein affinities for small molecules: Conceptions and misconceptions. Arch Biochem Biophys 1979; 193: 314-328). The stoichiometric two-site binding model measures the concentrations the plasma albumin ($A_{Total}$), the total bilirubin ($B_{Total}$) and the non-albumin bound or free bilirubin ($B_{Free}$) measured at multiple $B_{Total}$ and uses them to determine the two equilibrium association constants for the albumin molecules binding one ($K_1$) and those binding two bilirubin molecules ($K_2$). In this model the $B_{Total}$ is the sum of the concentrations of albumin binding one ($A:B_1$) and twice that binding two bilirubin molecules ($2 \times A:B_2$) plus $B_{Free}$ and the $A_{Total}$ is the sum of $A:B_1+A:B_2+$the concentration of unoccupied or free albumin binding sites ($A_{Free}$) binding no bilirubin. The chemical equilibrium is:

$$A_{Free} + B_{Free}$$

$$A{:}B_1 + 2A{:}B_2,$$

and the mass action equations are:

$$\frac{A{:}B_1 + 2A{:}B_2}{A_{Total}} \cong \frac{B_{Total}}{A_{Total}} = \text{Molar Ratio} \cong \frac{K_1 B_{Free} + 2K_1 K_2 B_{Free}^2}{1 + K_1 B_{Free} + K_1 K_2 B_{Free}^2}$$

which can be solved for $B_{Free}$ using the equation below wherein MR is the molar ratio:

$$B_{Free} = \frac{\left(-K_1(MR-1) \pm \sqrt{K_1(MR-1)^2 - 4(K_1 K_2 MR(MR-2))}\right)}{2K_1 K_2 (MR-2)}$$

Non-linear regression analysis of the molar ratios versus the $B_{Free}$ from TABLE 3 were used to determine the best fit $K_1$ (0.93 dL/µg) and $K_2$ (0.04 dL/µg) using the stoichiometric equation $$\text{Molar Ratio} \cong \frac{K_1 B_{Free} + 2K_1 K_2 B_{Free}^2}{1 + K_1 B_{Free} + K_1 K_2 B_{Free}^2}.$$

FIG. 7 compares the calculated $B_{Free}$ at 1 mg/dL $B_{Total}$ increments using $$B_{Free} = \frac{B_{Total}}{K_A (B_{Tmsx} - B_{Total})}$$

using the $B_{Tmax}$ (36.9 mg/dL) and $K_A$ (0.57) obtained from the pairing the $B_{Total}$ of 8.3 mg/dL with $B_{Total}$ of 31.3 mg/dL in Table 3 versus $$B_{Free} = \frac{\left(-K_1(MR-1) \pm \sqrt{K_1(MR-1)^2 - 4(K_1 K_2 MR(MR-2))}\right)}{2K_1 K_2 (MR-2)}$$

and shows that the novel method for quantifying bilirubin binding compares quite favorably with the standard stochiometric method for quantifying binding. The clear advantage of the novel method is that it provides robust binding analysis yet requires only two data points and no measurement of $A_{Total}$ and therefore much less time and materials for the measurements needed to quantify bilirubin binding.

A more clinically applicable approach to quantifying bilirubin binding is to consider both how much ($B_{Tmax}$) and how "tightly" ($K_A$) bilirubin can be bound as unknowns and derive these unknowns from $B_{Total}$ and $B_{Free}$ measurements. This requires a novel approach to the routine measurement of $B_{Total}$ and $B_{Free}$, which is to measure $B_{Total}$ and $B_{Free}$ in a plasma sample before and after enrichment of the sample with bilirubin.

The plasma equilibrium concentrations at any given plasma $B_{Total}$ and (unknown) $B_{Tmax}$ are:

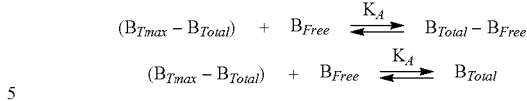

wherein $B_{Tmax}$ is how much bilirubin can be bound, $B_{Tmax} - B_{Total}$ is the concentration of available (unoccupied) bilirubin binding sites, and $B_{Total} - B_{Free}$ is the concentration of bilirubin bound to plasma binding sites (since $B_{Free}$ is orders of magnitude less than $B_{Total}$, bound bilirubin = $B_{Total} - B_{Free} \cong B_{Total}$).

The mass action equation is $$B_{Free} = \frac{B_{Total}}{K_A (B_{Tmax} - B_{Total})}$$

wherein $B_{total}$ and $B_{Free}$ are measured and $B_{Tmax}$ and $K_A$ are unknown. If $B_{Total}$ and $B_{Free}$ are measured before and after sample enrichment with bilirubin to give measured values $B_{Total}$, $B_{Free}$ and $B_{Total\_2}$, $B_{Free\_2}$, two equations with two unknowns ($B_{Tmax}$ and $K_A$) are provided that can be solved for $B_{Tmax}$ and $K_A$ as shown below.

$$B_{Tmax} = \frac{B_{Total} \cdot B_{Total\_2} (B_{Free\_2} - B_{Free})}{B_{Total} \cdot B_{Free\_2} - B_{Total} \cdot B_{Free\_1}}$$

The calculated $B_{Tmax}$, $B_{Total}$, and $B_{Free}$ are then entered into $$B_{Free} = \frac{B_{Total}}{K_A (B_{Tmsx} - B_{Total})}$$

to obtain $$K_A = \frac{B_{Total}}{B_{Free} (B_{Tmsx} - B_{Total})},$$

or alternatively, $K_A$ is the negative intercept and $B_{Tmax}$ is the negative slope divided by the intercept of $$\frac{1}{B_{Free}} \text{ versus } \frac{1}{B_{Total}}$$

as the reciprocal of $$B_{Free} = \frac{B_{Total}}{K_A (B_{Tmsx} - B_{Total})}$$

is the linear equation $$\frac{1}{B_{Free}} = \frac{B_{Tmax} \cdot K_A}{B_{Total}} - K_A.$$

The clinically relevant quantification of bilirubin binding are the mass action variables above ($B_{Total}$, $B_{Free}$, $B_{Total\_2}$, $B_{Free\_2}$, $B_{Tmax}$, and $K_A$) constitute a Bilirubin Binding Panel (BBP). Optionally, $B_{Tmax}$ and $K_A$ can be used to determine whether a newborn binds bilirubin normally. TABLE 4 below shows $B_{Tmax}$ and $K_A$ determined before and after adding sulfisoxazole (sulfa) to a bilirubin/human albumin sample containing 3.0 g/dL albumin, which about doubles the $B_{Free}$ and significantly changes $B_{Tmax}$ and $K_A$. A newborn less than (<) 28 weeks gestation with a $B_{Total}$ of 8.3, $B_{Free}$ of 0.51 µg/dL, $B_{Tmax}$ of 24.3 mg/dL and $K_A$ of 1.01 per Tables 1 and 2 would reach the exchange transfusion $B_{FreeStandard}$ of 1.51 µg/dL (FIG. 6) at when the $B_{Total}$ reaches $$\frac{B_{FreeStandard} \cdot K_A \cdot B_{Tmax}}{1+(K_A \cdot B_{FreeStandard})} = \frac{1.51 \frac{\mu g}{dL} \cdot 1.01 \frac{dL}{\mu g} \cdot 24.3 \frac{mg}{dL}}{1+\left(1.01 \frac{dL}{\mu g} \cdot 1.51 \frac{\mu g}{dL}\right)} = 24.2 \text{ mg}/dL,$$

but if $B_{Tmax}$ is 42.1 mg/dL and $K_A$ is 0.20 dL/ug, $$\frac{1.51 \frac{\mu g}{dL} \cdot 0.20 \frac{dL}{\mu g} 42.1 \frac{mg}{dL}}{1+\left(0.20 \frac{dL}{\mu g} 1.51 \frac{\mu g}{dL}\right)} = 9.8 \text{ mg}/dL$$

showing the much risk of BIND despite identical $B_{Total}$ of 8.3 mg/dL.

TABLE 4

|  | $B_{Total}$ mg/dL | $B_{Total\_2}$ mg/dL | $B_{Free}$ µg/dL | $B_{Free1\_2}$ µg/dL | $B_{Tmax}$ mg/dL | $K_A$ dL/µg |
|---|---|---|---|---|---|---|
| No sulfa | 8.3 | 11.7 | 0.51 | 0.92 | 24.3 | 1.01 |
| + sulfa | 8.3 | 12.3 | 1.22 | 2.05 | 42.1 | 0.20 |

Measuring Total and Unbound Bilirubin ($B_{Total}$ and $B_{Free}$): The peroxidase test (see, e.g., Jacobsen J, Wennberg R P. Determination of unbound bilirubin in the serum of newborns. Clin Chem 1974; 20:783-789) measures both $B_{Total}$ and $B_{Free}$. This test is used clinically in Japan. In alternative embodiments, novel modifications of methods as provided herein measure $B_{Free}$ at two horseradish peroxidase levels to accurately determine $B_{Free}$ and measure $B_{Total}$ and $B_{Free}$ before and after bilirubin enrichment of a plasma or other blood sample to provide $B_{Tmax}$ and $K_A$ to complete the Bilirubin Binding Panel (BBP) described herein. The BBP quantifies bilirubin binding ($B_{Tmax}$ and $K_A$) and the risk of BIND using $B_{FreeStandard}$ determined for a comparable population. The peroxidase test is based on the horse radish peroxidase (HRP) catalyzed oxidation of bilirubin by peroxide. Bilirubin absorbs light maximally at 440 nm when no albumin is present and at 460 nm when bound to albumin. Bilirubin bound to albumin is protected from oxidation and only $B_{Free}$ is oxidized. The light absorbance at 440 nm (no albumin) or 460 nm (albumin present) decreases as bilirubin is oxidized, and the reaction rate constant, Kp, can be determined using known bilirubin and HRP concentrations in solutions without albumin present (i.e. all the bilirubin is unbound or "free") as shown in the equivalent velocity equations below:

$$-\frac{dB_{Total}}{dt} = K_p \cdot HRP \cdot B_{Total}.$$

-continued $$-\frac{d\text{Absorbance 440 nm}}{dt} = K_p \cdot HRP \cdot \text{Absorbance 440 nm.}$$

DETERMINATION OF $K_P$: FIG. 8 graphically illustrates the change in bilirubin absorbance per second (s) at 440 nm and 460 nm during HRP catalyzed oxidation of bilirubin by peroxide without albumin present as recorded using an HP8452 computer directed spectrophotometer (reaction: 3.0 mL of 0.1 M phosphate buffer, pH 7.4 containing 128 µmol/L $H_2O_2$, 25 µL HRP with reaction [HRP]=0.061 µg/mL, 5 µL of 1 mg/mL bilirubin solution with reaction [$B_{Total}$]=163 µg/dL, 1 cm path length cuvette, 30° C.).

The $K_P \cdot HRP$ for the reaction is easily calculated by integrating the velocity equation above between times t=0 and t=t:—

$$-\int_0^t \frac{dB_{Total}}{dt} = \int_0^t K_p \cdot HRP \cdot B_{Total}$$

$$\ln\left(\frac{B_{Total}}{B_{Total \text{ at } t=0}}\right) = \ln\left(\frac{\text{Absorbance 440 nm}}{\text{Absorbance 440 nm at } t=0}\right) = -K_p \cdot HRP \cdot t$$

$K_p \cdot HRP$ is the negative slope of the $$\ln\left(\frac{\text{Absorbance 440 nm}}{\text{Absorbance 440 nm at } t=0}\right)$$

versus time, which divided by the reaction HRP concentration provides the $K_p$.

DETERMINATION OF $B_{Total}$ AND $B_{Free}$: FIG. 9 graphically illustrates light absorbance at 460 nm as a function of time in seconds and shows the change in bilirubin absorbance at 460 nm in a bilirubin-albumin solution before and after adding HRP and peroxide as recorded using an HP8452™ computer directed spectrophotometer. The initial absorbance at 460 nm is used to obtain $B_{Total}$ and the change in absorbance at 460 nm after adding HRP/peroxide is used to obtain the $B_{Free}$ as described below.

The standard reaction is conducted in a 1 cm path cuvette containing 1.0 mL of 0.1 M phosphate buffer, pH 7.4 to which 25 µL of sample (e.g. plasma or serum), followed by 25 µL of HRP (typically 1.5 mg/mL) and 5 µL of 26 mmol/f $H_2O_2$ to provide a reaction $H_2O_2$ of 120 µmol/L $H_2O_2$. $B_{Total}$ is calculated from the absorbance prior to adding HRP and $H_2O_2$ and $B_{Free}$ from the change in absorbance following addition of HRP/$H_2O_2$ as further described below. The novel changes to the method involve repeating the test at another HRP concentration (typically using 0.75 mg/mL) and then enriching the sample with bilirubin (typically to increase the $B_{Total}$ by 5 to 20 mg/dL) and repeating the test again at two HRP concentrations.

$B_{Total}$ is calculated by dividing the initial absorbance by the known extinction coefficient (0.827/cm light path length for $B_{Total}$ in mg/mL) and $B_{Free}$ is calculated from the change in absorbance at 460 nm after adding HRP/$H_2O_2$. Since only $B_{Free}$ is oxidized (bound bilirubin is protected from oxidation), the velocity equation is $$-\frac{dB_{Total}}{dt} = K_p \cdot HRP \cdot B_{Free}.$$

However, the equilibrium $B_{Free}$ falls to an unknown lower steady state free bilirubin ($B_{Fss}$) as the oxidation of $B_{Free}$ disrupts the equilibrium from $$(B_{Tmax} - B_{Total}) + B_{Free} \overset{K_A}{\rightleftharpoons} B_{Total}, \text{ to } (B_{Tmax} - B_{Total}) + B_{Fss} + H_2O_2 \overset{HRP}{\underset{K_A}{\rightleftharpoons}} B_{Total} + \text{oxidized bilirubin}$$

and, therefore $$-\frac{dB_{Total}}{dt} = K_p \cdot HRP \cdot B_{Fss}$$

wherein:

$$B_{Fss} = \frac{B_{Total}}{K_A(B_{Tmax} - B_{Total}) + K_p \cdot HRP},$$

and the integrated velocity is:

$$\int_0^t \frac{dB_{Total}}{dt} = -\int_0^t K_p \cdot HRP \cdot B_{Fss} = -\int_0^t \frac{K_p \cdot HRP \cdot B_{Total}}{K_A(B_{Tmax} - B_{Total}) + K_p \cdot HRP},$$

or $$\int_0^t \frac{dB_{Total}}{B_{Total}} = -\int_0^t \frac{K_p \cdot HRP}{K_A(B_{Tmax} - B_{Total}) + K_p \cdot HRP} dt$$

$$\ln\left(\frac{B_{Total}}{B_{Total} \text{ at } t=0}\right) = -\frac{K_p \cdot HRP}{K_A(B_{Tmax} - B_{Total}) + K_p \cdot HRP} t \text{ and}$$

$$B_{Fss} = \frac{-B_{Total} \cdot \text{Slope}}{Kp \cdot HRP}$$

wherein $$\text{Slope} = -\frac{K_p \cdot HRP}{K_A(B_{Tmax} - B_{Total}) + K_p \cdot HRP}$$

obtained from ln $$\left(\frac{B_{Total}}{B_{Total} \text{ at } t=0}\right)$$

versus t.

$B_{Free}$ is obtained by measuring $B_{Fss}$ at the additional HRP concentration and using $$\frac{1}{B_{Fss}} = \frac{K_A(B_{Tmax} - B_{Total})}{B_{Total}} + \frac{K_p \cdot HRP}{B_{Total}},$$

which is the reciprocal of the $B_{Fss}$ equation above to obtain the intercept of $1/B_{Fss}$ versus $$HRP\left(\frac{K_A(B_{Tmax} - B_{Total})}{B_{Total}}\right),$$

the reciprocal of which is $B_{Free}$ $$\left(B_{Free} = \frac{B_{Total}}{K_A(B_{Tmsx} - B_{Total})}\right)$$

The sample is enriched with bilirubin and $B_{Total\_2}$ and $B_{Free\_2}$ are measured and used with the pre-enrichment $B_{Total}$ and $B_{Free}$ to obtain $B_{Tmax}$ and $K_A$ as seen in TABLES 2 and 3.

$$B_{Free} = \frac{B_{Total}}{K_A(B_{Tmax} - B_{Total})}$$

can then be readily solved by for $B_{Tmax}$ and $K_A$ using two equations with two unknowns ($B_{Tmax}$ and $K_A$) and solving for $B_{Tmax}$ as shown below:

$$B_{Tmax} = \frac{B_{Total}B_{Total\_2}(B_{Free\_2} - B_{Free})}{B_{Total}B_{Free\_2} - B_{Total\_2}B_{Free}}$$

The calculated $B_{Tmax}$, $B_{Total}$, and $B_{Free}$ are then entered into $$B_{Free} = \frac{B_{Total}}{K_A(B_{Tmsx} - B_{Total})}$$

to obtain $$K_A = \frac{B_{Total}}{B_{Free}(B_{Tmsx} - B_{Total})},$$

or alternatively, $K_A$ is the negative intercept and $B_{Tmax}$ is the negative slope divided by the intercept of $$\frac{1}{B_{Free}} \text{ versus } \frac{1}{B_{Total}}$$

as the reciprocal of $$B_{Free} = \frac{B_{Total}}{K_A(B_{Tmsx} - B_{Total})}$$

is the linear equation $$\frac{1}{B_{Free}} = \frac{B_{Tmax} \cdot K_A}{B_{Total}} - K_A$$

The Bilirubin Binding Panel:

The components of bilirubin binding are linked mathematically by the mass action equation $$B_{Free} = \frac{B_{Total}}{K_A(B_{Tmsx} - B_{Total})},$$

which makes no assumptions about the stoichiometric or chemical nature of the actual plasma bilirubin binding sites, yet the constants $B_{Tmax}$ and $K_A$ provide accurate estimates of $B_{Free}$ at $B_{Total}$ below $B_{Tmax}$ as illustrated in FIGS. 5 and 7. In one embodiment, the peroxidase test measures serum or plasma $B_{Total}$ and $B_{Free}$, e.g., as described by Jacobsen J. Wennberg R P. Determination of unbound bilirubin in the serum of newborns. Clin Chem 1974; 20:783-789. In alternative embodiments, $B_{Free}$ is measured at a second peroxidase concentration to insure accurate measurement of $B_{Free}$ and the sample is then enriched with bilirubin and the test repeated at the higher $B_{Total}$ and $B_{Free}$ to provide $B_{Tmax}$ and $K_A$ using two equations and two unknowns or using linear analysis of $$\frac{1}{B_{Free}} = \frac{K_A \cdot B_{Tmax}}{B_{Total}} - K_A$$

wherein the negative of the intercept=–intercept=$K_A$, and the negative of the $$\text{slope/intercept} = \frac{-\text{slope}}{\text{intercept}} = \frac{-K_A \cdot B_{Tmax}}{-K_A} = B_{Tmax}.$$

An individual's $B_{Tmax}$ and $K_A$ are compared with, optionally the median $B_{Tmax}$ and $K_A$ for the comparable population to determine whether the individual has normal bilirubin binding. The risk of BIND is increased if the individual's $B_{Free}$ is greater than or equal to a $B_{FreeStandard}$ for the population that is determined determine whether the individual has normal bilirubin binding. The risk of BIND is increased if the individual's $B_{Free}$ is greater than or equal to a $B_{FreeStandard}$ for the population that is determined using current $B_{Total}$ treatment guidelines and optionally the population's median $B_{Tmax}$ and $K_A$, e.g. for newborns less than (<) 28 weeks gestation per Table 1, at the mandatory exchange transfusion $B_{Total}$ of 14 mg/dL and the median $B_{Tmax}$ (22.0 mg/dL) and $K_A$ (1.16 dL/µg) for the 31 newborns in Table 2, $$B_{FreeStandard} = \frac{B_{Total}\left(14\frac{mg}{dL}\right)}{K_A\left(1.16\frac{dL}{\mu g}\right)\left(B_{Tmsx}\left(22.0\frac{mg}{dL}\right) - B_{Total}\left(14\frac{mg}{dL}\right)\right)} 1.51 \, \mu g/dL,$$

and if an individual's $B_{Free}$ is equal to or greater than (≥) $B_{FreeStandard}$ treatment is warranted irrespective of the $B_{Total}$, and if $B_{Free}$ is less than $B_{FreeStandard}$, the individual's unique $B_{Total}$ at which $B_{FreeStandard}$ occurs and treatment is needed can be obtained using the individual's $B_{Tmax}$, $K_A$, and $B_{FreeStandard}$ as $$B_{Total} = \frac{B_{Tmax} \cdot K_A \cdot B_{FreeStandard}}{1 + (K_A \cdot B_{FreeStandard})}.$$

$B_{Tmax}$ and $K_A$ robustly quantify how well the plasma binds bilirubin as they quantify how much ($B_{Tmax}$) and how tightly ($K_A$) plasma binds bilirubin. Comparing $B_{Tmax}$ and $K_A$ in a newborn with $B_{Tmax}$ and $K_A$ in a population of peers (e.g. comparing them with the median $B_{Tmax}$ and $K_A$) determines how well that newborn binds bilirubin compared with its peers, just as any blood test in a patient is compared with normal values in the population to detect underlying conditions. If the newborn's $B_{Free}$ is equal to or exceeds $B_{FreeStandard}$ the population as described above, treatment is warranted irrespective of the $B_{Total}$. If the newborn's $B_{Free}$ is less than $B_{FreeStandard}$ the unique $B_{Total}$ at which that newborn should be treated is obtained from the $B_{FreeStandard}$ and that newborn's $B_{Tmax}$ and $K_A$ as shown above. This approach reduces the uncertainties in the current treatment guidelines that use $B_{Total}$ alone (see FIG. 1) and individualizes care.

$B_{Tmax}$ and $K_A$ population parameters (mean, standard deviation, median, etc.) can be readily obtained in the various newborn populations (term, premature <28 weeks as shown in Table 2, ill, etc.) to provide the population specific bilirubin binding data needed to augment treatment decisions that are currently based solely on $B_{Total}$.

Devices: Zone Fluidics Analytical Instruments

The manual peroxidase test as originally described to measure $B_{Total}$ and $B_{Free}$ requires 25 µL sample, and for the four tests described herein ($B_{Total}$ and $B_{Free}$ measured at two peroxidase concentrations before and after bilirubin enrichment) would require 100 µL of sample. Novel herein are technologies that automate the tests and reduce sample volumes.

In alternative embodiments, provided are devices and systems comprising automated micro-fluid handling technologies such as zone fluidics systems, and the appropriate chemistry, e.g., robotic chemistry, for the handling and manipulation of samples, e.g., serum, plasma or whole blood samples from patients, for measuring: total serum bilirubin concentration ($B_{Total}$) and unbound bilirubin or free bilirubin concentration ($B_{Free}$) from a plasma or blood sample (Jacobsen J, Wennberg R P. Determination of unbound bilirubin in the serum of newborns. Clin Chem 1974; 20:783, Ahlfors C E, et. al. Measurement of unbound bilirubin by the peroxidase test using Zone Fluidics Clin Chim Acta 2006; 365:78), and also incorporating—directly in the device or indirectly as a multiplexed system operatively connected to the device—computer-implemented methods as provided herein to analyze this data and output a maximum bilirubin concentration ($B_{Tmax}$) and a bilirubin binding constant ($K_A$), which when compared to the product in a population of peers accurately determines how well a patient binds bilirubin and whether the risk of bilirubin-induced neurological dysfunction (BIND) as measured by the $B_{Free}$ is greater than the risk at $B_{FreeStandard}$ for the population of peers.

In alternative embodiments, provided are devices comprising Sequential Injection Analysis (SIA) and/or Zone Fluidics technology, and equivalent automated micro-fluid handling technologies, for handling and analyzing patient blood, serum, or plasma and expanding these technologies to include titration with bilirubin to enable calculation of $B_{Tmax}$ and $K_A$.

In alternative embodiments, provided are devices comprising components, e.g., robotic chemistry components, for measuring: total serum bilirubin concentration ($B_{Total}$); unbound bilirubin or free bilirubin concentration ($B_{Free}$) from a sample, e.g., a plasma, serum, or a blood sample. Any chemistry, device or robotic chemistry component known in the art can be used or incorporated into a device as used and/or provided herein, e.g., as described in U.S. Pat. No. 7,939,333 (describing metal enhanced fluorescence-based sensing methods); U.S. Pat. No. 7,767,467 (describing e.g., methods and device for the separation of small particles or cells from a fluid suspension); U.S. Pat. No. 7,416,896 (describing e.g., methods and devices for determining total and bound plasma bilirubin); U.S. Pat. No. 7,625,762 (describing e.g., methods and device for the separation of small particles or cells from a fluid suspension); U.S. Pat. No. 6,887,429 (describing e.g., methods and apparatus for the automation of existing medical diagnostic tests); U.S. Pat. No. 6,692,702 (describing e.g., methods and apparatus for utilizing a filtration device for removing interferants from a sample containing cells in an automated apparatus); and, U.S. Pat. No. 6,613,579; or, as described in U.S. patent publications: e.g., U.S. Pat App no. 2018/0045723 A1 (describing e.g., lateral flow devices and methods for analyzing a fluid sample); U.S. Pat App no. 2018/0052093 A1 (describing e.g., devices and methods for analyzing particles in a sample); U.S. Pat App no. 2016/0245799; or, as described in: Amin, S. B., Clinical Perinatology 43 (2016) 241-257 (describing e.g., a peroxidase method for measuring plasma bilirubin binding); Ahlfors, et al., Clinical Biochemistry 40 (2007) 261-267 (describing e.g., effects of sample dilution, peroxidase concentration, and chloride ion on the measurement of unbound bilirubin in premature newborns); Ahlfors, C. E., Analytical Biochemistry 279, 130-135 (2000) (describing e.g., measurement of plasma unbound unconjugated bilirubin; Ahlfors, et al., Clinica Chimica Acta 365 (2006) 78-85 (describing, e.g., measurement of unbound bilirubin by the peroxidase test using Zone Fluidics); Wennberg et al., Pediatrics 117 (2006) 474-485; or, WO 2013032953 A2, Huber et al, Clinical Chemistry 58 (2012) 869-876 (describing e.g., fluorescent probes that undergo fluorescence quenching when binding bilirubin to quantify unbound bilirubin).

In alternative embodiments, provided are devices having the capacity to output or send relevant data to a device-incorporated or separate device or system for executing a computer implemented method as provided herein, which then calculates and outputs: bilirubin binding constant, maximum total bilirubin concentration, and the clinically relevant diagnostic product $B_{Tmax}$-$K_A$ obtained from the measured components of the Bilirubin Binding Panel described above.

In alternative embodiments, provided are Zone Fluidics systems having flow manifolds that are simple and robust, e.g., comprising a pump, selection valve, and detector connected by micro-bore tubing. The same manifold can be used for widely different chemistries simply by changing the flow program rather than the plumbing architecture and hardware. In alternative embodiments, provided are Zone Fluidics acting as a fluidics analytical robotic system. In alternative embodiments, specific strengths of this exemplary embodiment of a microfluidics technology that can include one, several or all of the following characteristics or advantages:

- can process sample volumes in the lower microliter range;
- can add bilirubin to a sample to enable measurement of $B_{Total}$ and $B_{Free}$ before and after sample bilirubin enrichment.
- can achieve the performance of high-end clinical chemistry systems or robotically enabled systems at a significantly lower price point;
- can achieve scalability to a point of care instrument—low cost of goods sold;
- can be computer controlled and automated;
- can be easily developed with modified methods—the flexibility in workflow; and
- kinetics enables the method to be optimized to produce the highest quality data without limitations from the hardware design;
- can fully automate complex methods;
- can provide improved reliability and easy maintenance;
- can drastically reduce reagent use (many other methods typically use 1 to 100 mL of reagents per measurement)—SIA typically uses 1 to 100 µL per measurement.

In alternative embodiments, a Zone Fluidics system as described in U.S. Pat. No. 7,416,896, or apparatus or components as described in U.S. Pat App no. US 2016/0245799, are used to practice alternative device embodiments as provided herein.

Computer Systems for Executing Computer-Implemented Methods:

In alternative embodiments, provided are computer-implemented methods to analyze laboratory data and output a Bilirubin Binding Panel including $B_{Total}$ and $B_{Free}$ before and after bilirubin enrichment of plasma or blood sample, the maximum $B_{Total}$ ($B_{Tmax}$) and the bilirubin binding constant ($K_A$) that provide the clinically relevant $B_{Tmax}$ and $K_A$ to compare with $B_{Tmax}$ and $K_A$ from the population of peers to determine whether bilirubin binding is normal, whether the risk of BIND is increased in a patient ($B_{Free}$ is equal to or greater than $B_{FreeStandard}$), and if not, the unique $B_{Total}$ for that patient at which treatment is warranted. The computer-implemented methods are executed using e.g., non-transitory computer readable medium, including e.g., use of a computer or processor, which may be incorporated into a device as provided herein, or separately but operatively connected to the device, e.g., as a system.

Alternative embodiments, including computer-implemented methods, are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing", "computing", "calculating", "determining", "displaying" or the like, refer to the actions and processes of a computer system, or similar electronic computing device that manipulates and transforms data represented as physical (e.g., electronic) quantities within the computer system's registers and memories into other data similarly represented as physical quantities within the computer system memories or registers or other such information storage, transmission, or display devices.

In alternative embodiments, provided are apparatus for performing the operations or computer implemented methods provided herein. This apparatus may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The algorithms and displays presented herein are not inherently related to any particular computer or other apparatus. Various general-purpose systems may be used with programs in accordance with the teachings herein, or it may prove convenient to construct a more specialized apparatus to perform the method steps. The structure for a variety of these systems will appear from the description below. In addition, embodiments provided herein are not described with reference to any particular programming language. It will be appreciated that a variety of programming languages may be used to implement the teachings of embodiments as described herein.

In alternative embodiments, a machine-readable medium includes any mechanism for storing or transmitting information in a form readable by a machine (e.g., a computer). For example, a machine-readable medium includes a machine-readable storage medium (e.g., read only memory ("ROM"), random access memory ("RAM"), magnetic disk storage media, optical storage media, flash memory devices, etc.), a machine-readable transmission medium (electrical, optical, acoustical or other form of propagated signals (e.g., carrier waves, infrared signals, digital signals, etc.)), etc.

In alternative embodiments, methods as provided herein are implemented in a computer system within which a set of instructions, for causing the machine to perform any one or more of the protocols or methodologies as provided herein may be executed. In alternative embodiments, the machine may be connected (e.g., networked) to other machines in a LAN, an intranet, an extranet, or the Internet, or any equivalents thereof. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. The term "machine" shall also be taken to include any collection of machines that individually or jointly execute a set (or multiple sets) of instructions to perform any one or more of the methodologies discussed herein.

In alternative embodiments, an exemplary computer system as provided herein comprises a processing device (processor), a main memory (e.g., read-only memory (ROM), flash memory, dynamic random-access memory (DRAM) such as synchronous DRAM (SDRAM) or Rambus DRAM (RDRAM), etc.), a static memory (e.g., flash memory, static random-access memory (SRAM), etc.), and a data storage device, which communicate with each other via a bus.

In alternative embodiments, a processor represents one or more general-purpose processing devices such as a microprocessor, central processing unit, or the like. More particularly, the processor may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor may also be one or more special-purpose processing devices such as an application specific integrated circuit (ASIC), a field programmable gate array (FPGA), a digital signal processor (DSP), network processor, or the like. In alternative embodiments the processor is configured to execute the instructions (e.g., processing logic) for performing the operations and steps discussed herein.

In alternative embodiments the computer system further comprises a network interface device. The computer system also may include a video display unit (e.g., a liquid crystal display (LCD) or a cathode ray tube (CRT)), an alphanumeric input device (e.g., a keyboard), a cursor control device (e.g., a mouse), and a signal generation device (e.g., a speaker).

In alternative embodiments, the data storage device (e.g., drive unit) comprises a computer-readable storage medium on which is stored one or more sets of instructions (e.g., software) embodying any one or more of the protocols, methodologies or functions as provided herein. The instructions may also reside, completely or at least partially, within the main memory and/or within the processor during execution thereof by the computer system, the main memory and the processor also constituting machine-accessible storage media. The instructions may further be transmitted or received over a network via the network interface device.

In alternative embodiments the computer-readable storage medium is used to store data structure sets that define user identifying states and user preferences that define user profiles. Data structure sets and user profiles may also be stored in other sections of computer system, such as static memory.

In alternative embodiments, while the computer-readable storage medium in an exemplary embodiment is a single medium, the term "machine-accessible storage medium" can be taken to include a single medium or multiple media (e.g., a centralized or distributed database, and/or associated caches and servers) that store the one or more sets of instructions. In alternative embodiments the term "machine-accessible storage medium" can also be taken to include any medium that is capable of storing, encoding or carrying a set of instructions for execution by the machine and that cause the machine to perform any one or more of the methodologies as provided herein. In alternative embodiments the term "machine-accessible storage medium" shall accordingly be taken to include, but not be limited to, solid-state memories, and optical and magnetic media.

Treating BIND and Hyperbilirubinemia

In alternative embodiments, provided are methods for treating, ameliorating, reversing or preventing in an individual in need thereof (optionally a jaundiced newborn or infant):

significant hyperbilirubinemia (optionally jaundice) or bilirubin toxicity, optionally bilirubin neurotoxicity, or a bilirubin-induced neurologic dysfunction (BIND), a bilirubin-induced neurodevelopmental impairment, or a neurodevelopmental impairment having toxic levels of bilirubin as a causative agent, optionally in a newborn, optionally comprising an encephalopathy or kernicterus, or sudden neurotoxicity (acute bilirubin encephalopathy), or choreoathetotic cerebral palsy, impairment having toxic levels of bilirubin as a causative agent, optionally in a newborn, optionally comprising an encephalopathy or kernicterus, or sudden neurotoxicity (acute bilirubin encephalopathy, or choreoathetotic cerebral palsy, a bilirubin-induced hearing impairment, or a hearing impairment having toxic levels of bilirubin as a causative agent, a bilirubin-induced autism, or an autism having toxic levels of bilirubin as a causative agent, a bilirubin-induced high tone hearing loss, a bilirubin-induced paralysis of upward gaze, or a bilirubin-induced yellow staining of the teeth.

Methods as provided herein indicate when therapy should start (commence) on an individual in need thereof, and provide directions to the physician as to the need for an appropriate treatment for an individual in need thereof, for example, with a phototherapy and/or an exchange transfusion, when concurrent clinical circumstances do not indicate a high risk of BIND.

Furthermore, the methods as provided herein can be used to monitor treatment to determine that bilirubin levels have decreased sufficiently to substantially reduce the risk of BIND, and thus signaling to the physician that treatment can be modified, interrupted or stopped. If BIND is occurring without obvious symptoms, the methods as provided herein can alert clinicians, thus allowing for early treatment that may reverse or lessen the damage (see Johnson L, et al, Clinical report from the pilot USA kernicterus registry (1992-2004). J Perinatol 2009; 29: S25-45), wherein the patient may be a newborn infant, a child, or an adult (e.g. see Blaschke T F, et al, Crigler-Najjar syndrome: an unusual course with development of neurologic damage at age eighteen. Pediatr. Res. 1974; 8:573-890).

Thus, diagnostic and treatment methods as provided herein help solve the problem that symptoms of BIND are often confused with other conditions, for example, infection (see Ahlfors et al, Unbound bilirubin in a term newborn with kernicterus. Pediatrics 2003; 111: 1110-1112), and that symptoms of BIND are often absent in premature newborns (see Watchko J F et al. The enigma of low bilirubin kernicterus in premature infants: why does it still occur, and is it preventable? Semin Perinatol 2014; 38: 397-406).

Any method known the art can be used to treat or ameliorate, or prevent, significant hyperbilirubinemia such as jaundice, bilirubin toxicity including bilirubin neurotoxicity, a bilirubin-induced neurologic dysfunction (BIND), a bilirubin-induced neurodevelopmental impairment, or a neurodevelopmental impairment having toxic levels of bilirubin as a causative agent, optionally in a newborn, optionally comprising an encephalopathy or kernicterus, or sudden neurotoxicity (acute bilirubin encephalopathy), or choreoathetotic cerebral palsy; impairment having toxic levels of bilirubin as a causative agent, optionally in a newborn, optionally comprising an encephalopathy or kernicterus, or sudden neurotoxicity (acute bilirubin encephalopathy, or choreoathetotic cerebral palsy; a bilirubin-induced hearing impairment, or a hearing impairment having toxic levels of bilirubin as a causative agent; a bilirubin-induced autism, or an autism having toxic levels of bilirubin as a causative agent; a bilirubin-induced high tone hearing loss; a bilirubin-induced paralysis of upward gaze, and/or a bilirubin-induced yellow staining of the teeth.

For example, significant hyperbilirubinemia such as jaundice, for example, neonatal jaundice, may be treated with phototherapy, or colored light, which works by changing trans-bilirubin into the water-soluble cis-bilirubin isomer, or by exchange transfusions, which can involve repeatedly withdrawing small amounts of blood and replacing it with donor blood, thereby diluting the bilirubin and material antibodies. In alternative embodiments, intravenous immunoglobulin (IVIg) is used in situations where significant hyperbilirubinemia such as jaundice may be related to blood type differences between mother and baby. This condition results in the baby carrying antibodies from the mother that contribute to the rapid breakdown of the baby's red blood cells. Intravenous transfusion of an anti-maternal-Ig immunoglobulin may decrease the hyperbilirubinemia or jaundice and lessen the need for or the extent of exchange transfusion.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Any of the above aspects and embodiments can be combined with any other aspect or embodiment as disclosed here in the Summary and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Modifications of this invention will occur readily to those of ordinary skill in the art in view of these teachings. The above description is illustrative and not restrictive. This invention is to be limited only by the following claims, which include all such embodiments and modifications when viewed in conjunction with the above specification and accompanying drawings. The scope of the invention should, therefore, be determined not with reference to the above description, but instead should be determined with reference to the appended claims along with their full scope of equivalents.

What is claimed is:

1. A method for treating, ameliorating, reversing or preventing in an individual in need thereof:
   a hyperbilirubinemia or bilirubin toxicity,
   a bilirubin neurotoxicity,
   a bilirubin-induced neurodevelopmental impairment,
   a neurodevelopmental impairment having toxic levels of bilirubin as a causative agent,
   a sudden bilirubin-induced neurotoxicity,
   an acute bilirubin encephalopathy,
   a choreoathetotic cerebral palsy,
   a bilirubin-induced hearing impairment, or a hearing impairment having toxic levels of bilirubin as a causative agent,
   a bilirubin-induced autism, or an autism having toxic levels of bilirubin as a causative agent,
   a bilirubin-induced high tone hearing loss,
   a bilirubin-induced paralysis of upward gaze, or
   a bilirubin-induced yellow staining of the teeth,
   the method comprising:
   (a) determining whether bilirubin binding is normal, or below normal in the individual in need thereof by a method comprising:
      (i) providing or taking, or having provided, a plasma, blood or serum sample from the individual;
      (ii) measuring $B_{Total}$ and $B_{Free}$,
      (iii) enriching the plasma, blood or serum sample with bilirubin,
      (iv) measuring $B_{Total}$ and $B_{Free}$ in the bilirubin enriched plasma; and,
      (v) determining the maximum total bilirubin concentration ($B_{Tmax}$) and the equilibrium association constant ($K_A$),
   wherein if the individual's $B_{Tmax}$ and $K_A$ are below the mean, average, or median $B_{Tmax}$ and $K_A$ for a comparable population, the individual has poor or clinically inefficient bilirubin binding, and
   if the individual's $B_{Free}$ is equal to or greater than the $B_{FreeStandard}$ for the comparable population that occurs at a current treatment $B_{Total}$ this indicates the presence of a risk of BIND that is sufficient to warrant treatment, wherein $$B_{Free} = \frac{B_{Total}}{K_A(B_{Tmsx} - B_{Total})}$$

and $B_{Free}$ and $B_{Total}$ are the measured concentrations of non-albumin bound or free bilirubin and total bilirubin concentration, respectively, and measuring $B_{Total}$ and $B_{Free}$ before and after enrichment of the sample with bilirubin to obtain $B_{Total}$, $B_{Free}$ and $B_{Total\_2}$, $B_{Free\_2}$ to provide two equations with two unknowns ($B_{Tmax}$ and $K_A$), that are solved for $B_{Tmax}$ $$B_{Tmax} = \frac{B_{Total}B_{Total\_2}(B_{Free\_2} - B_{Free})}{B_{Total}B_{Free\_2} - B_{Total\_2}B_{Free}}$$

and the measured $B_{Total}$ and $B_{Free}$ are used with the calculated $B_{Tmax}$ to obtain $$K_A = \frac{B_{Total}}{B_{Free}(B_{Tmsx} - B_{Total})},$$

or $K_A$ is the negative intercept and $B_{Tmax}$ is the negative slope divided by the intercept of $$\frac{1}{B_{Free}} \text{ versus } \frac{1}{B_{Free}}$$

as the reciprocal of $$B_{Free} = \frac{B_{Total}}{K_A(B_{Tmsx} - B_{Total})}$$

is the linear equation $$\frac{1}{B_{Free}} = \frac{B_{Tmax} \cdot K_A}{B_{Total}} - K_A,$$

and
(b) commencing treating, ameliorating, reversing or preventing the individual in need thereof for:
   the jaundice or bilirubin toxicity,
   the bilirubin neurotoxicity,
   the bilirubin-induced neurodevelopmental impairment,
   the impairment having toxic levels of bilirubin as a causative agent,
   the acute bilirubin encephalopathy,
   the choreoathetotic cerebral palsy,
   the bilirubin-induced hearing impairment, or hearing impairment having toxic levels of bilirubin as a causative agent,
   the bilirubin-induced autism, or the autism having toxic levels of bilirubin as a causative agent,
   the bilirubin-induced high tone hearing loss,
   the bilirubin-induced paralysis of upward gaze, or
   the bilirubin-induced yellow staining of the teeth, if the individual in need thereof has a lower than normal calculated $B_{Tmax}$ and $K_A$ or a $B_{Free}$ equal to or greater than $B_{FreeStandard}$ as determined in step (a).

2. The method of claim 1, wherein in step (c) enriching the plasma, blood or serum sample with bilirubin comprises increasing the amount of bilirubin in the sample from between about 5 to 25 mg/dL, or to enrich $B_{Total}$ near the relevant current clinical threshold $B_{Total}$ for a relevant population.

3. The method of claim 1, wherein the individual in need thereof is a jaundiced newborn or infant.

4. The method of claim 1, wherein the significant hyperbilirubinemia comprises jaundice.

5. The method of claim 1, wherein the neurodevelopmental impairment having toxic levels of bilirubin as a causative agent comprises an encephalopathy or kernicterus.

6. The method of claim 1, wherein if the comparable population is a newborn less than 28 weeks gestation, the mean, average, or median $B_{Tmax}$ and $K_A$ for the comparable population is: the median $B_{Tmax}$ and $K_A$ of 22.0 mg/dL and 1.16 dL/µg.

7. The method of claim 2, wherein the relevant population comprises: the exchange transfusion threshold $B_{Total}$ of 14 mg/dL in newborns less than 28 weeks gestation, or the exchange transfusion threshold of 25 mg/dL in well term newborns.

8. The method of claim 1, wherein the treating, ameliorating, reversing or preventing is for jaundice or bilirubin toxicity.

9. The method of claim 1, wherein the treating, ameliorating, reversing or preventing is for bilirubin neurotoxicity.

10. The method of claim 1, wherein the treating, ameliorating, reversing or preventing is for bilirubin-induced neurodevelopmental impairment.

11. The method of claim 1, wherein the treating, ameliorating, reversing or preventing is for impairment having toxic levels of bilirubin as a causative agent.

12. The method of claim 1, wherein the treating, ameliorating, reversing or preventing is for acute bilirubin encephalopathy.

13. The method of claim 1, wherein the treating, ameliorating, reversing or preventing is for choreoathetotic cerebral palsy.

14. The method of claim 1, wherein the treating, ameliorating, reversing or preventing is for bilirubin-induced hearing impairment, or hearing impairment having toxic levels of bilirubin as a causative agent.

15. The method of claim 1, wherein the treating, ameliorating, reversing or preventing is for bilirubin-induced autism or for autism having toxic levels of bilirubin as a causative agent.

16. The method of claim 1, wherein the treating, ameliorating, reversing or preventing is for bilirubin-induced high tone hearing loss.

17. The method of claim 1, wherein the treating, ameliorating, reversing or preventing is for bilirubin-induced paralysis of upward gaze.

18. The method of claim 1, wherein the treating, ameliorating, reversing or preventing is for bilirubin-induced yellow staining of the teeth.

19. The method of claim 1, wherein the treating, ameliorating, reversing or preventing comprises phototherapy.

* * * * *